United States Patent [19]

Green et al.

[11] Patent Number: 4,576,165
[45] Date of Patent: Mar. 18, 1986

[54] SURGICAL LIGATION AND CUTTING DEVICE WITH SAFETY MEANS

[75] Inventors: David T. Green; Richard A. McGarry, both of Norwalk, Conn.

[73] Assignee: United States Surgical Corporation, Norwalk, Conn.

[21] Appl. No.: 573,066

[22] Filed: Jan. 23, 1984

[51] Int. Cl.[4] ............................................. A61B 17/11
[52] U.S. Cl. .................... 128/305; 128/325; 128/326; 128/334 R; 227/DIG. 1; 227/DIG. 1 B; 227/DIG. 1 C; 72/410; 29/243.56
[58] Field of Search .......... 128/305, 325, 326, 334 R; 227/DIG. 1, DIG. 1 B, DIG. 1 C; 72/410; 29/243.56

[56] References Cited

U.S. PATENT DOCUMENTS

| | | | |
|---|---|---|---|
| 3,545,444 | 12/1970 | Green | 128/305 |
| 3,584,628 | 6/1971 | Green | 128/305 |
| 3,665,924 | 5/1972 | Noiles et al. | 128/305 |
| 3,675,688 | 7/1972 | Bryan et al. | 128/305 |
| 3,735,762 | 5/1973 | Bryan et al. | 128/305 |
| 3,740,994 | 6/1973 | DeCarlo, Jr. | 29/243.56 |
| 3,844,289 | 10/1974 | Noiles | 128/334 R |
| 3,955,581 | 5/1976 | Spasiano et al. | 128/334 R |
| 4,086,926 | 5/1978 | Green et al. | 128/334 R |
| 4,319,576 | 3/1982 | Rothfuss | 128/305 |
| 4,349,028 | 9/1982 | Green | 128/305 |
| 4,492,232 | 1/1985 | Green | 227/DIG. 1 |
| 4,512,345 | 4/1985 | Green | 227/DIG. 1 |

Primary Examiner—John Doll
Assistant Examiner—Lance Johnson
Attorney, Agent, or Firm—Robert R. Jackson; John E. Nathan

[57] ABSTRACT

A surgical instrument for ligating and cutting body tissue restrained in the instrument is disclosed. To ligate the tissue, the instrument applies a pair of plastic clips at spaced apart locations on the tissue. The clips are advanced towards the tissue and separated from a pair of clip trains by a clip pusher mechanism operating over a predetermined path. A knife operating over another predetermined path then cuts the tissue between the spaced apart clips. A safety mechanism is actuated by the clip pusher mechanism in the event that a clip is not presented to the pusher mechanism. The safety mechanism, when actuated by the pusher mechanism, directly blocks the path of the knife. A latch mechanism is provided which locks tissue in the instrument to alert the surgeon that the pusher mechanism has jammed at the completion of a ligating and cutting operation.

34 Claims, 28 Drawing Figures

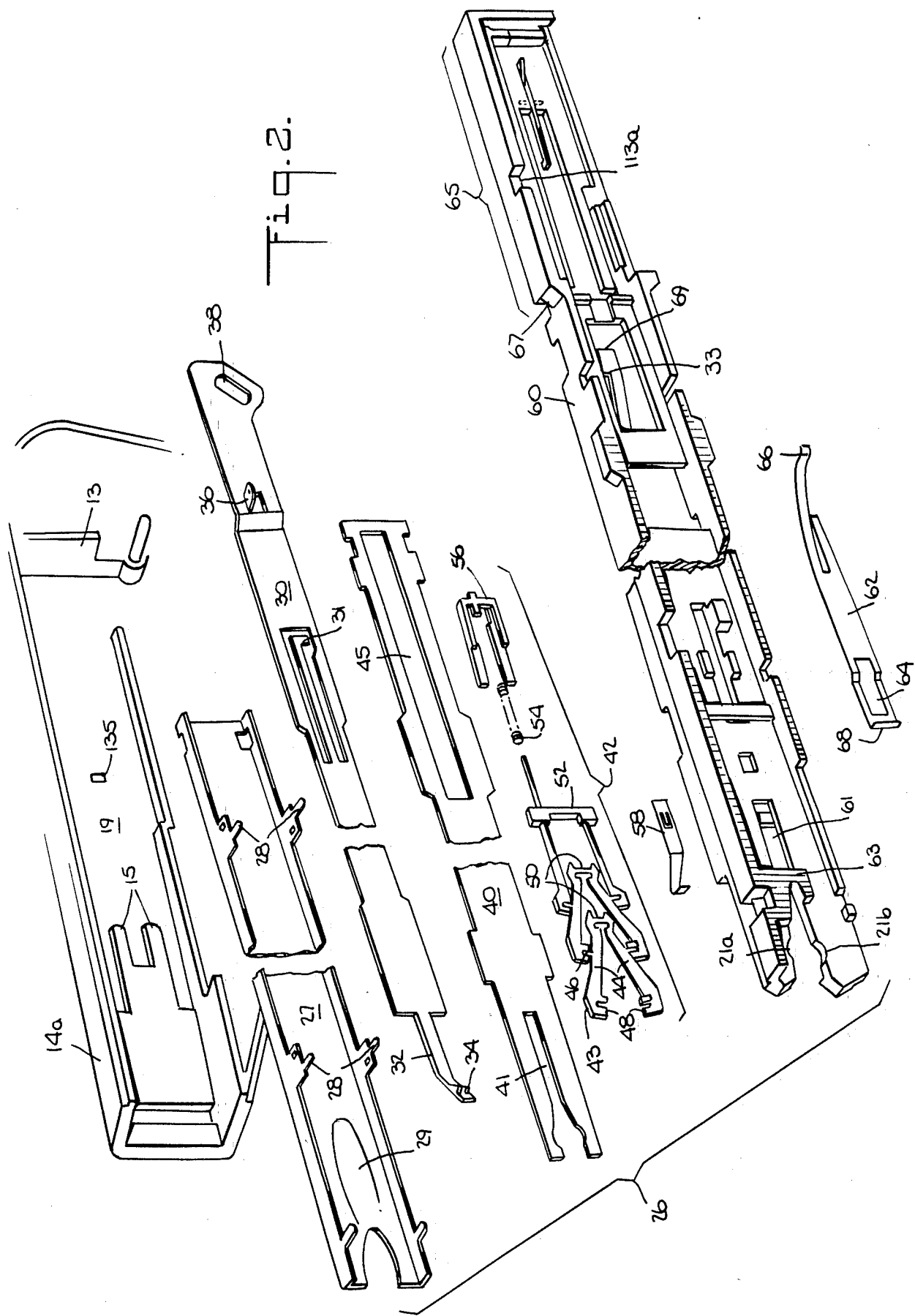

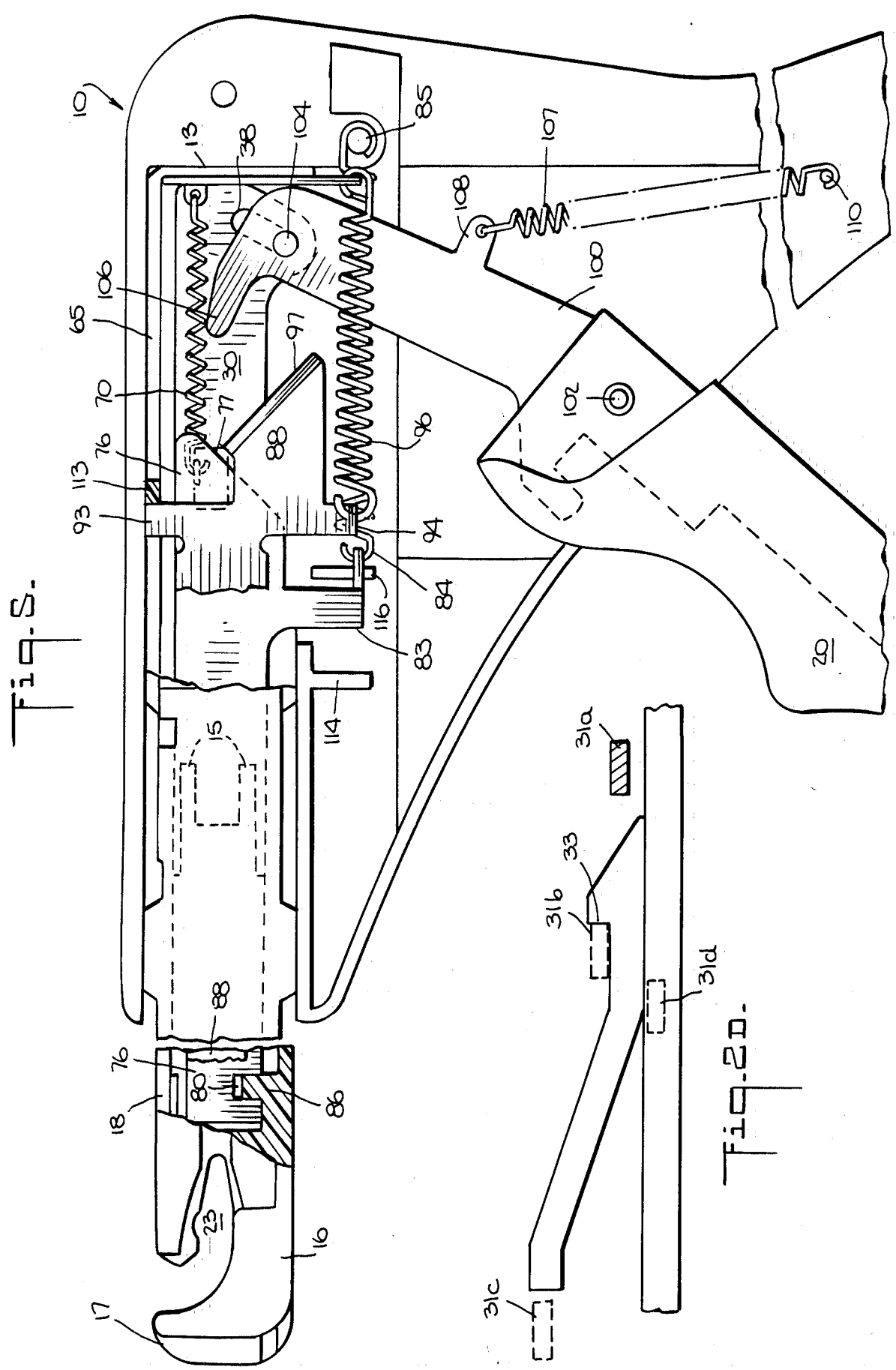

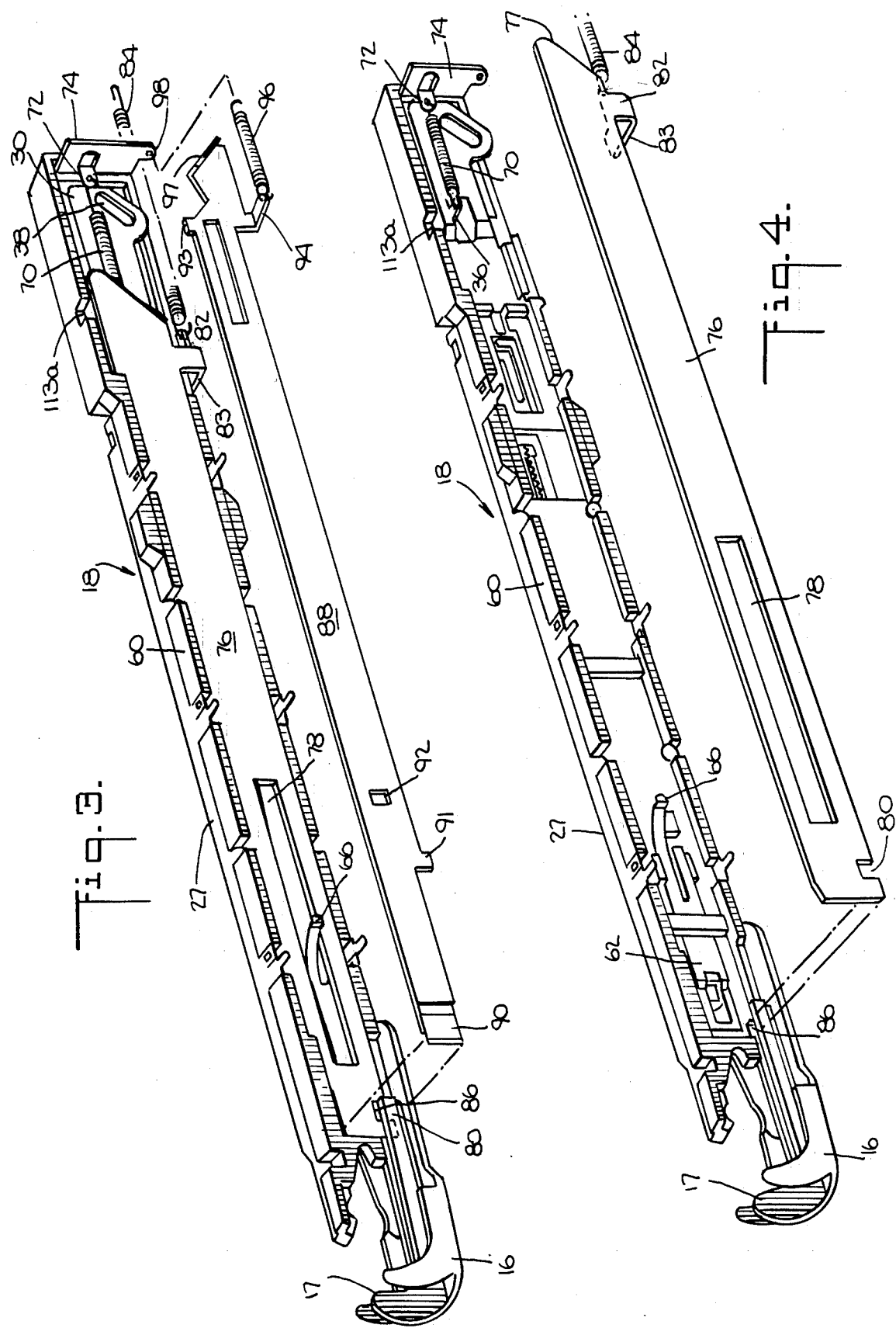

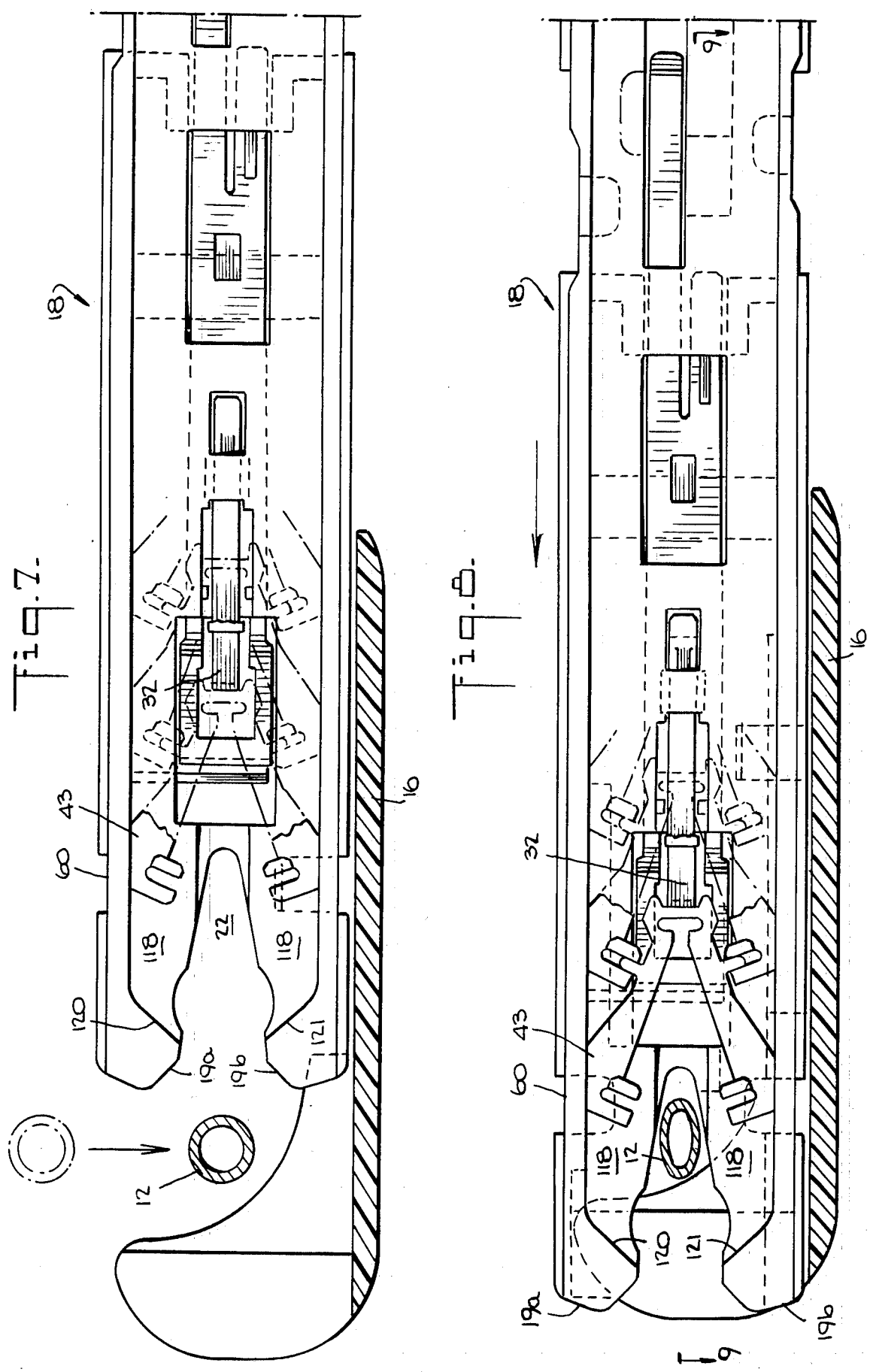

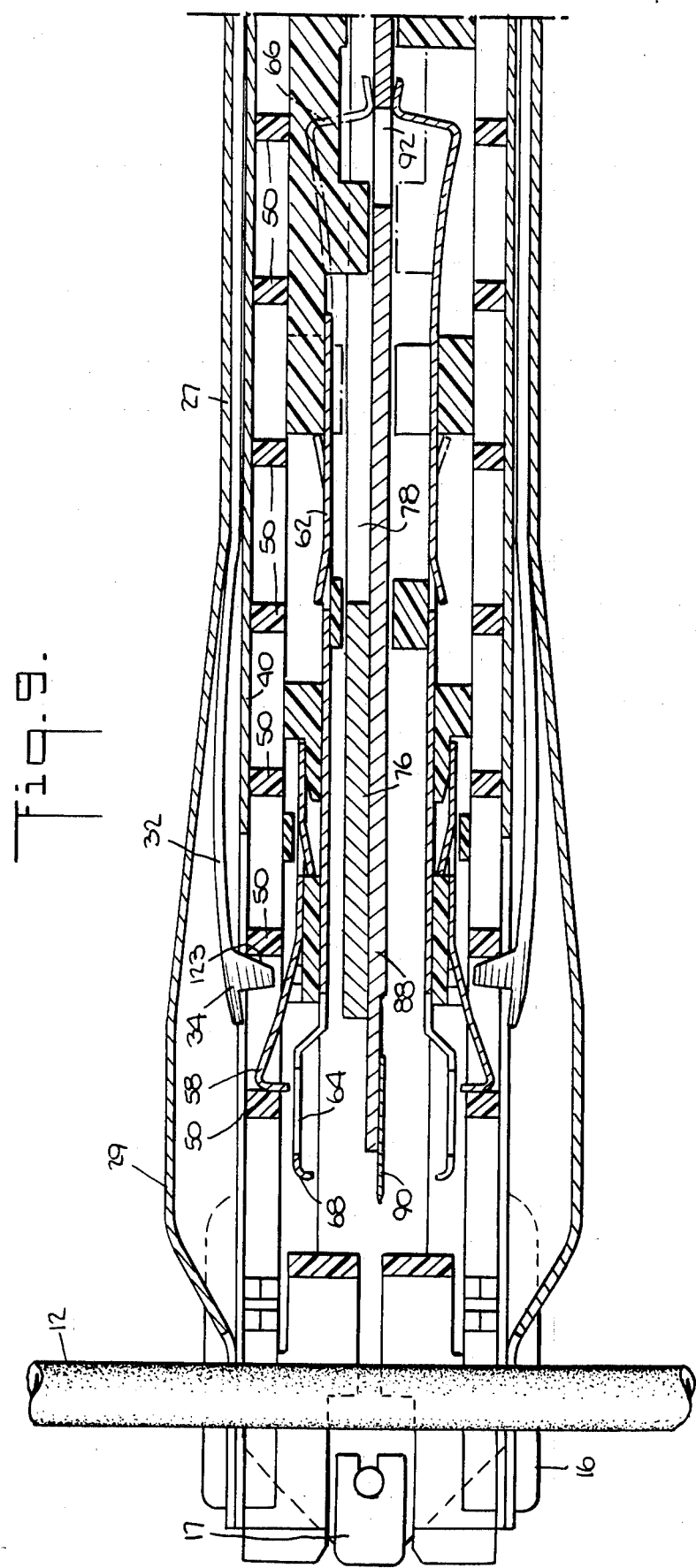

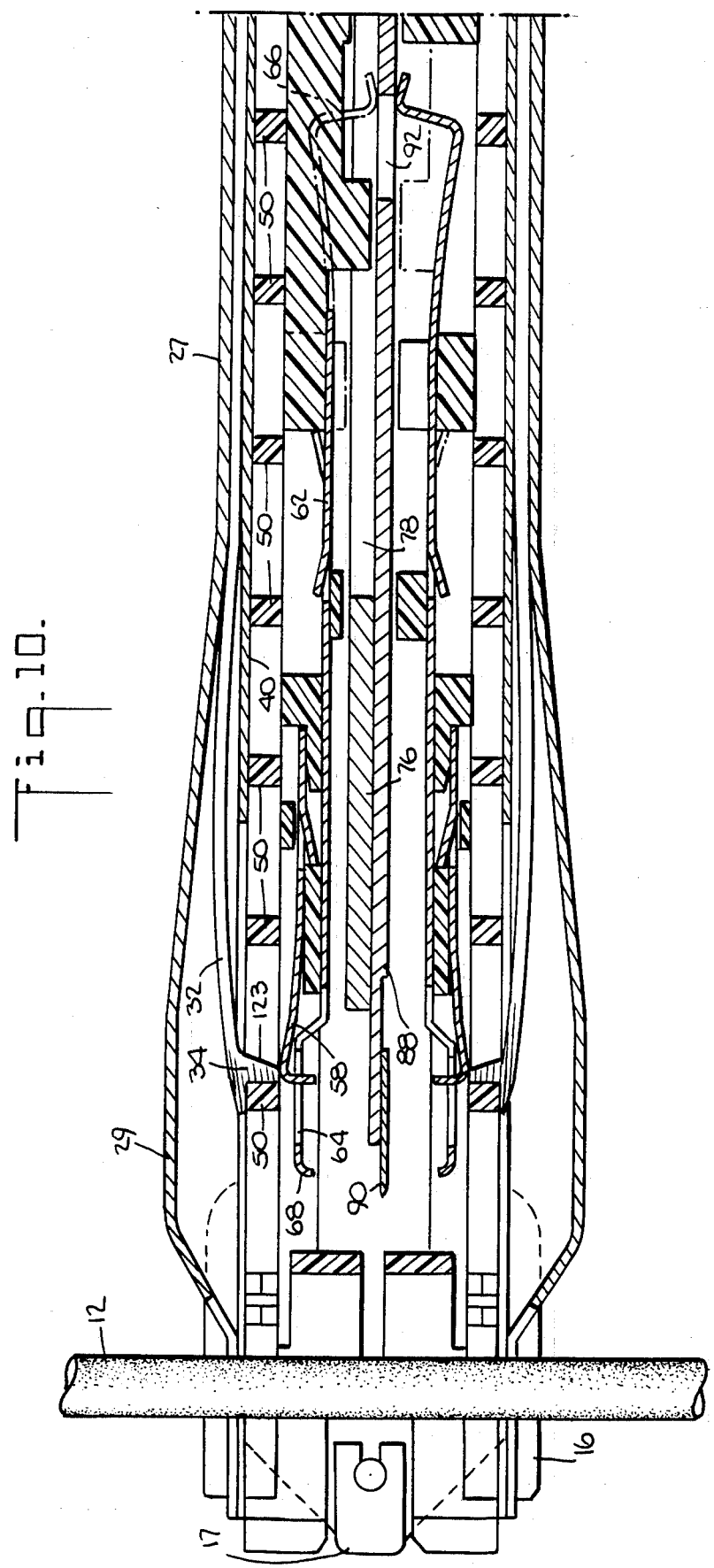

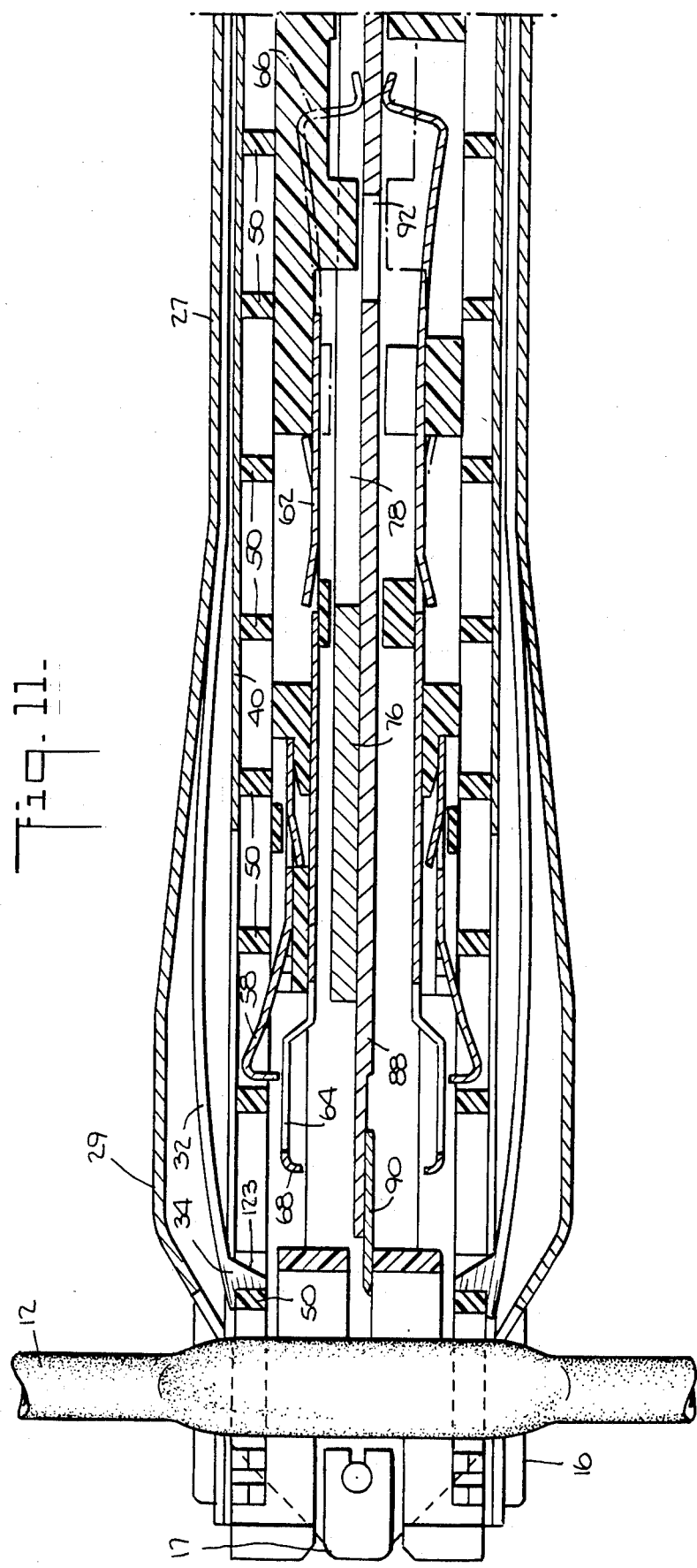

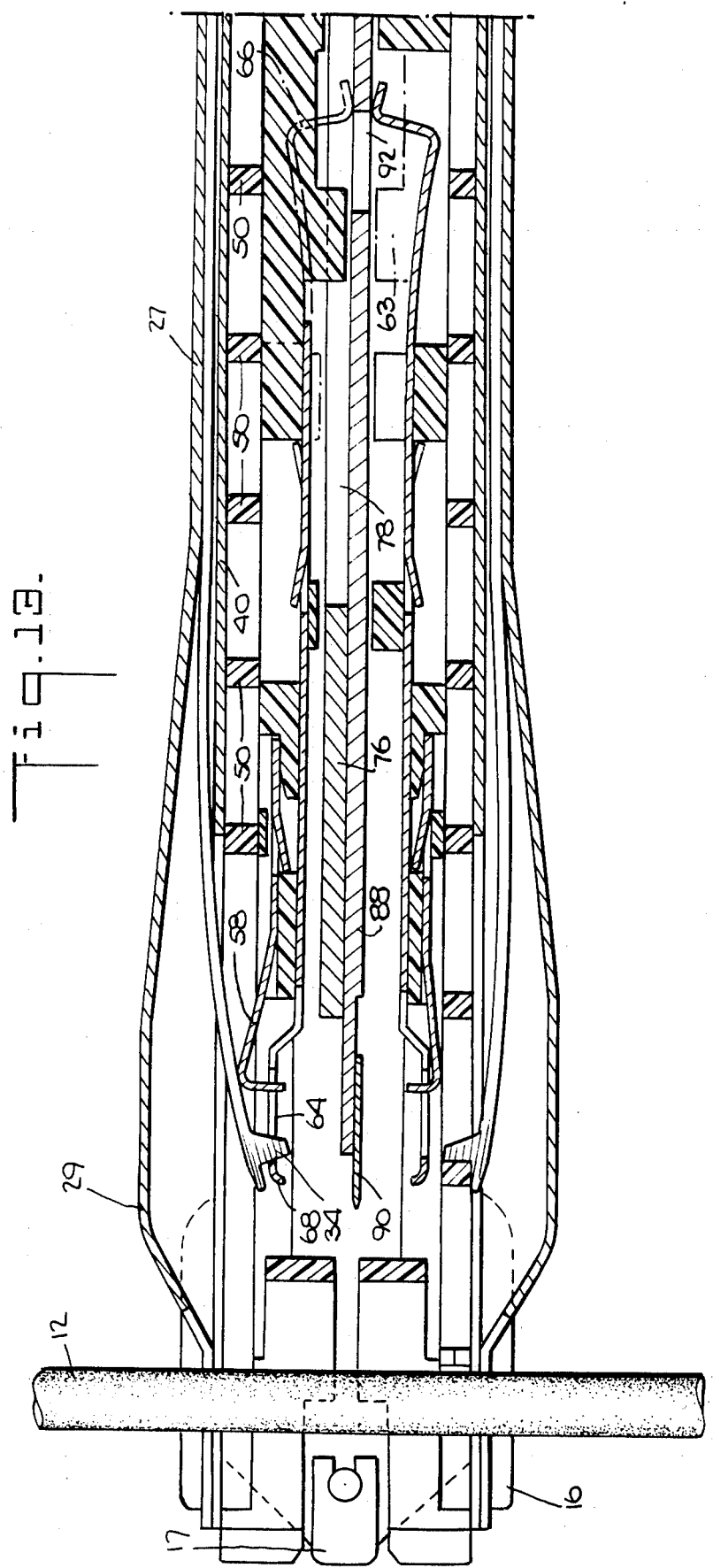

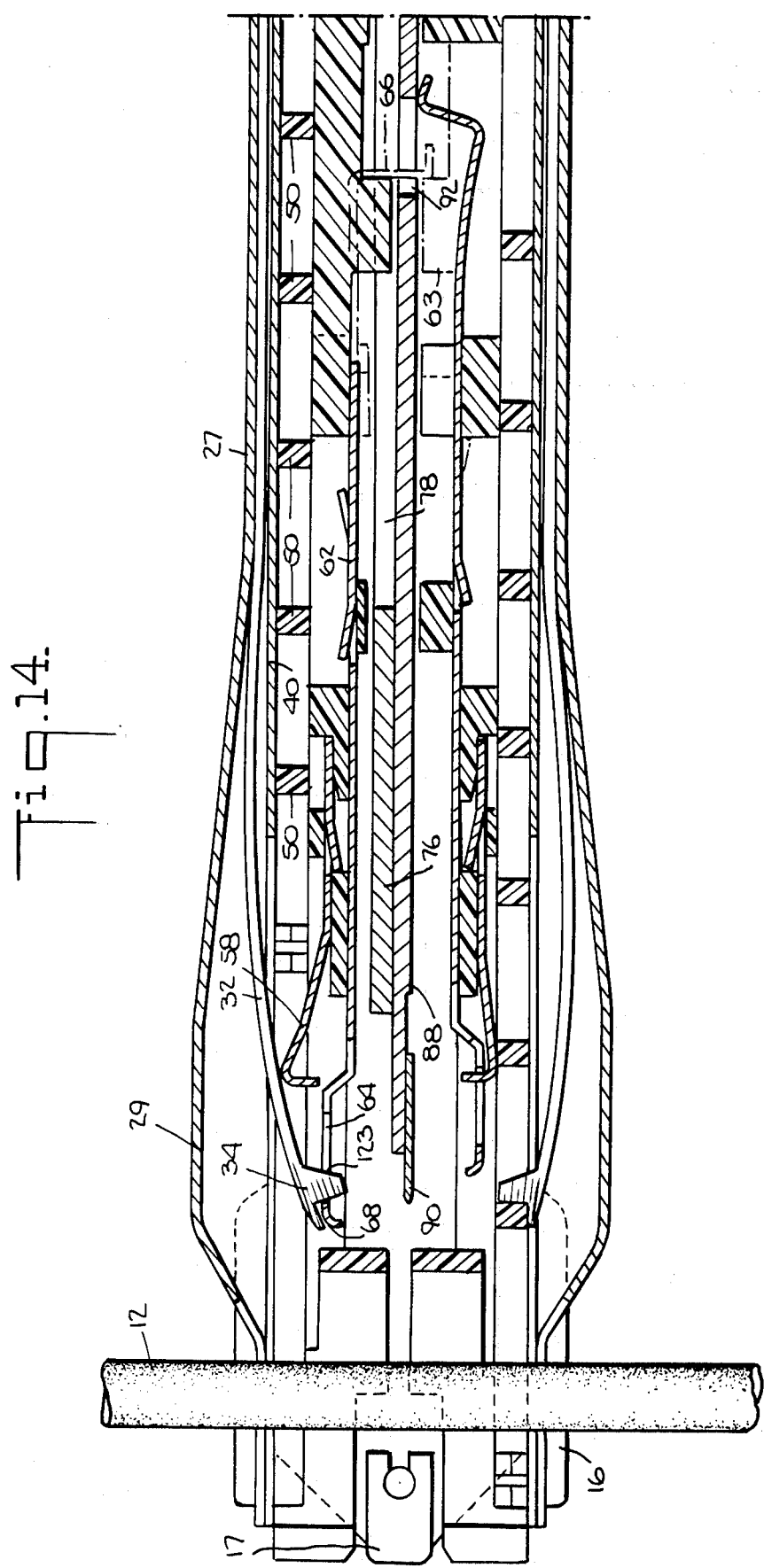

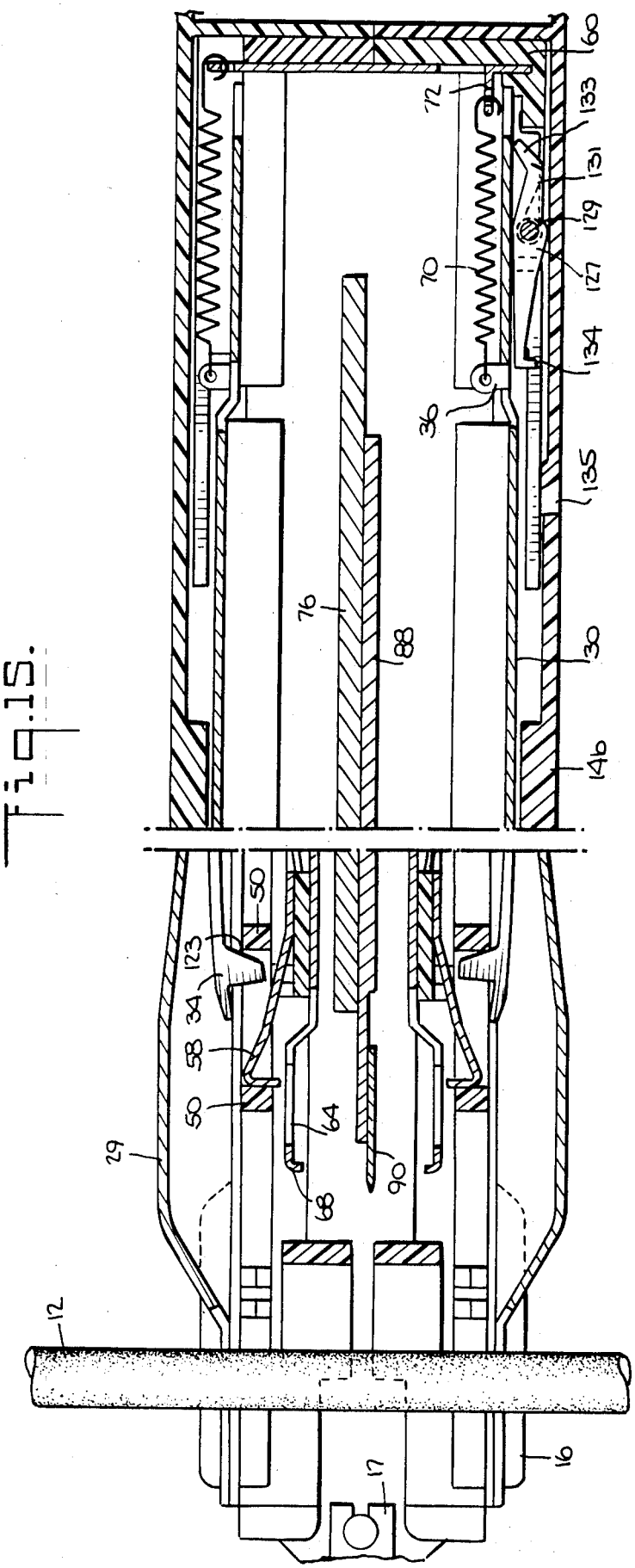

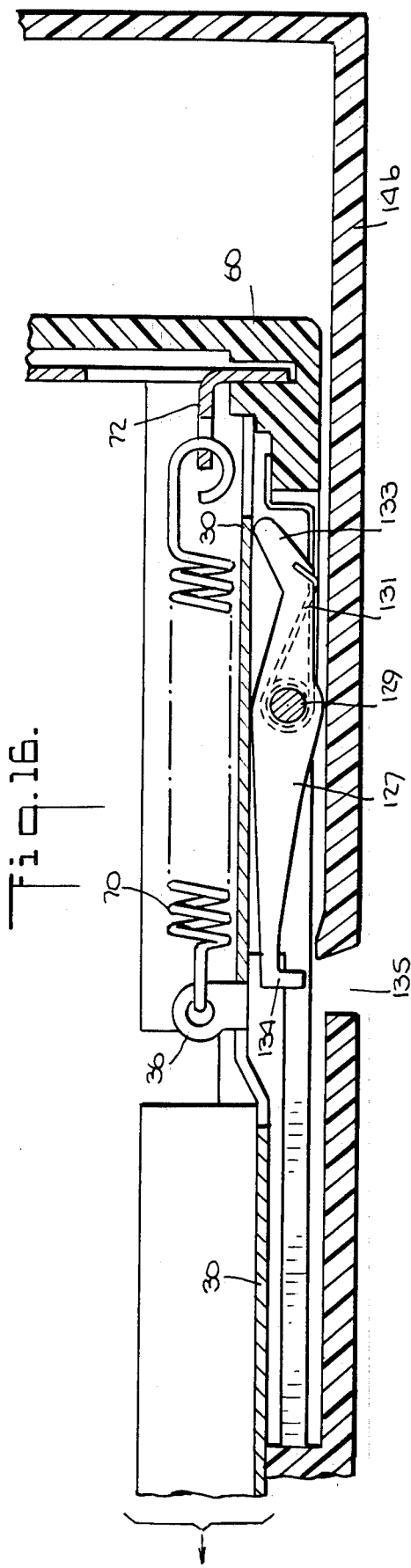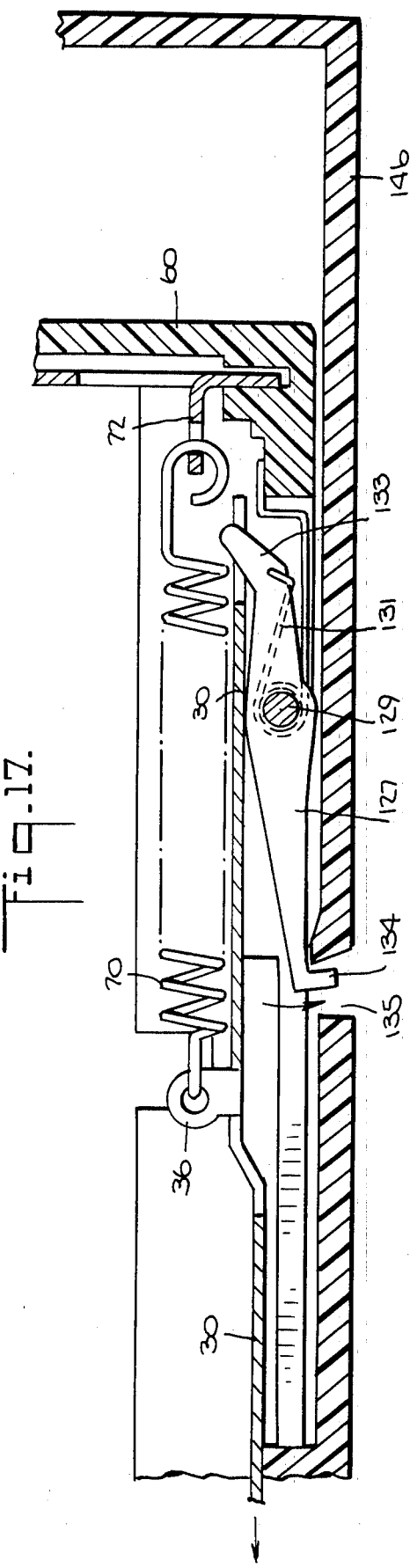

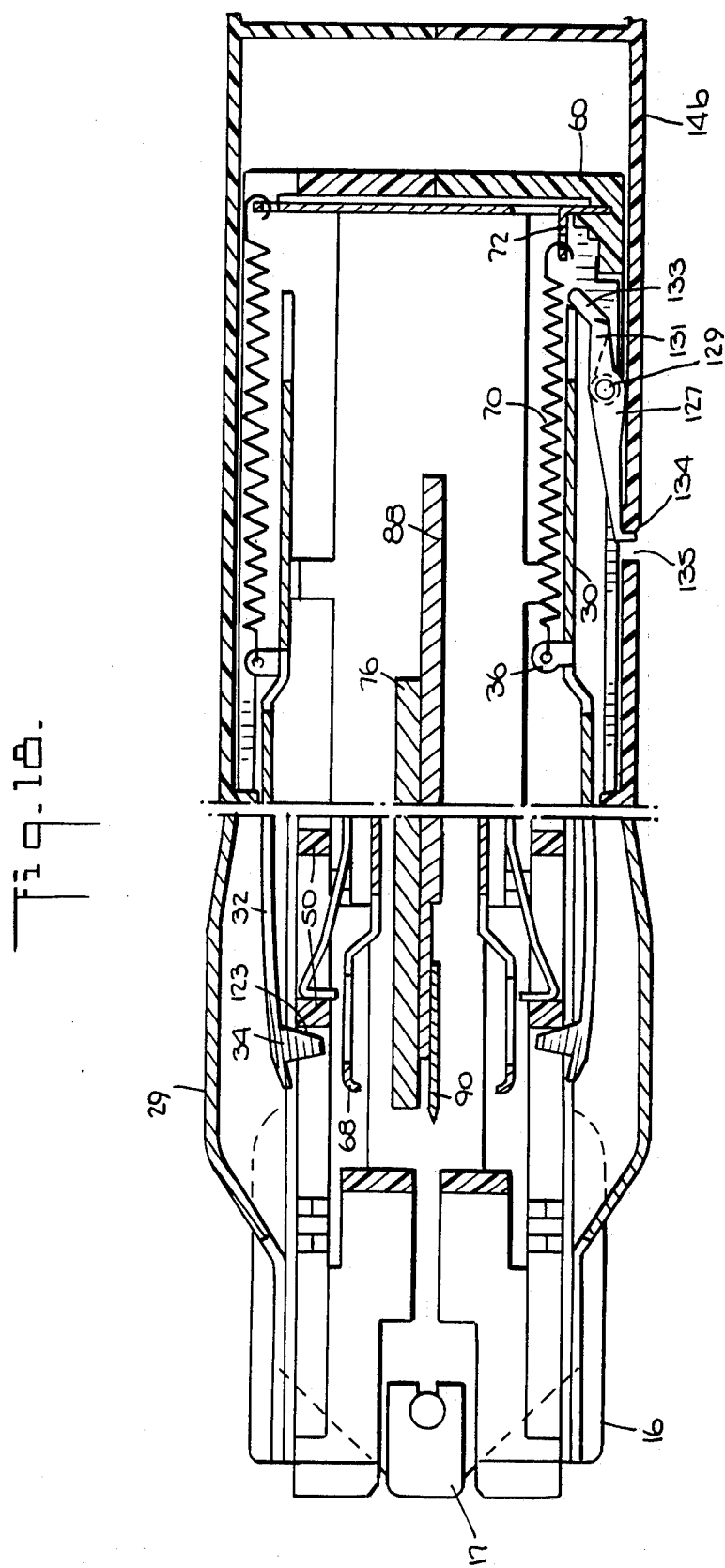

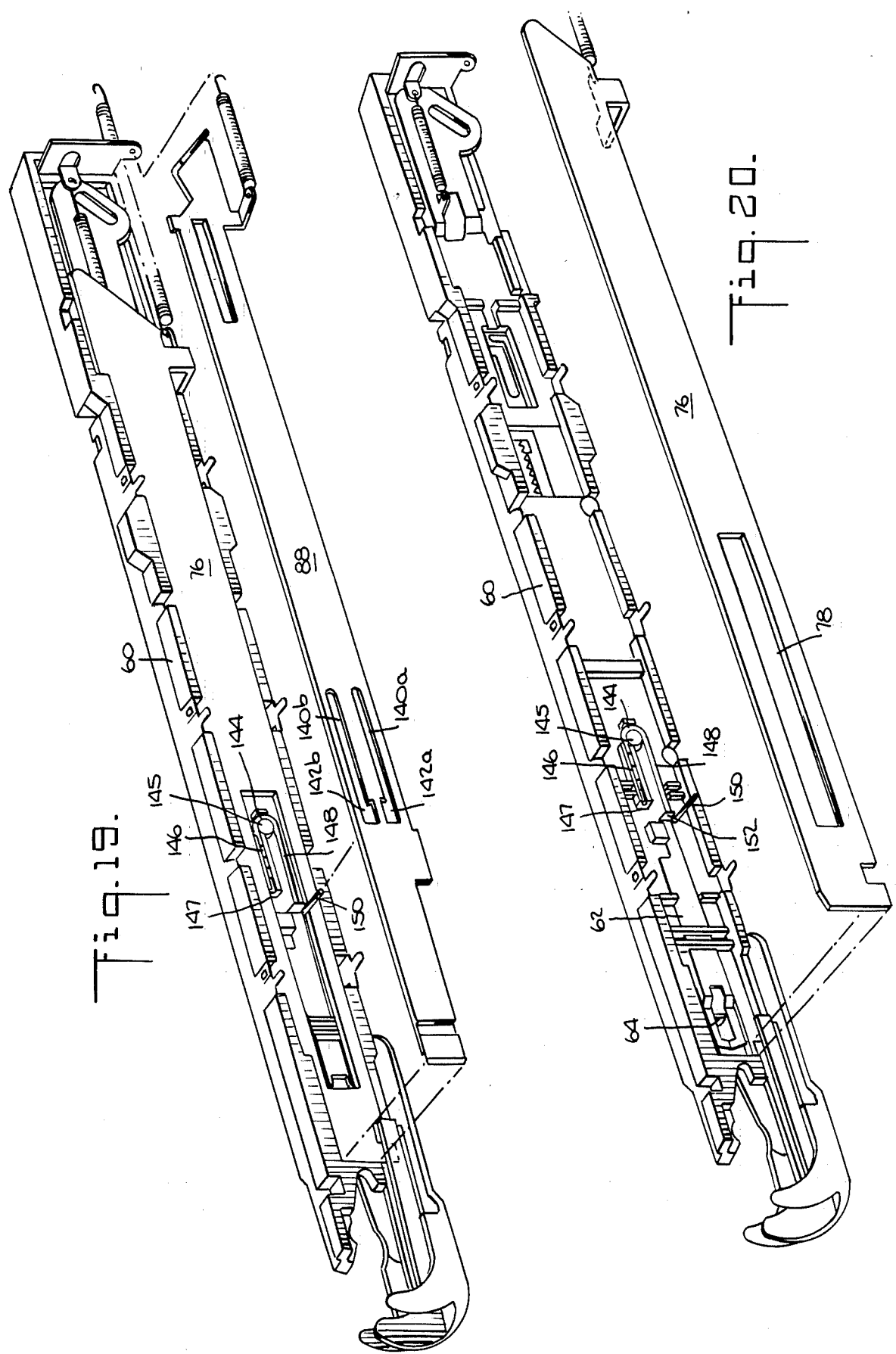

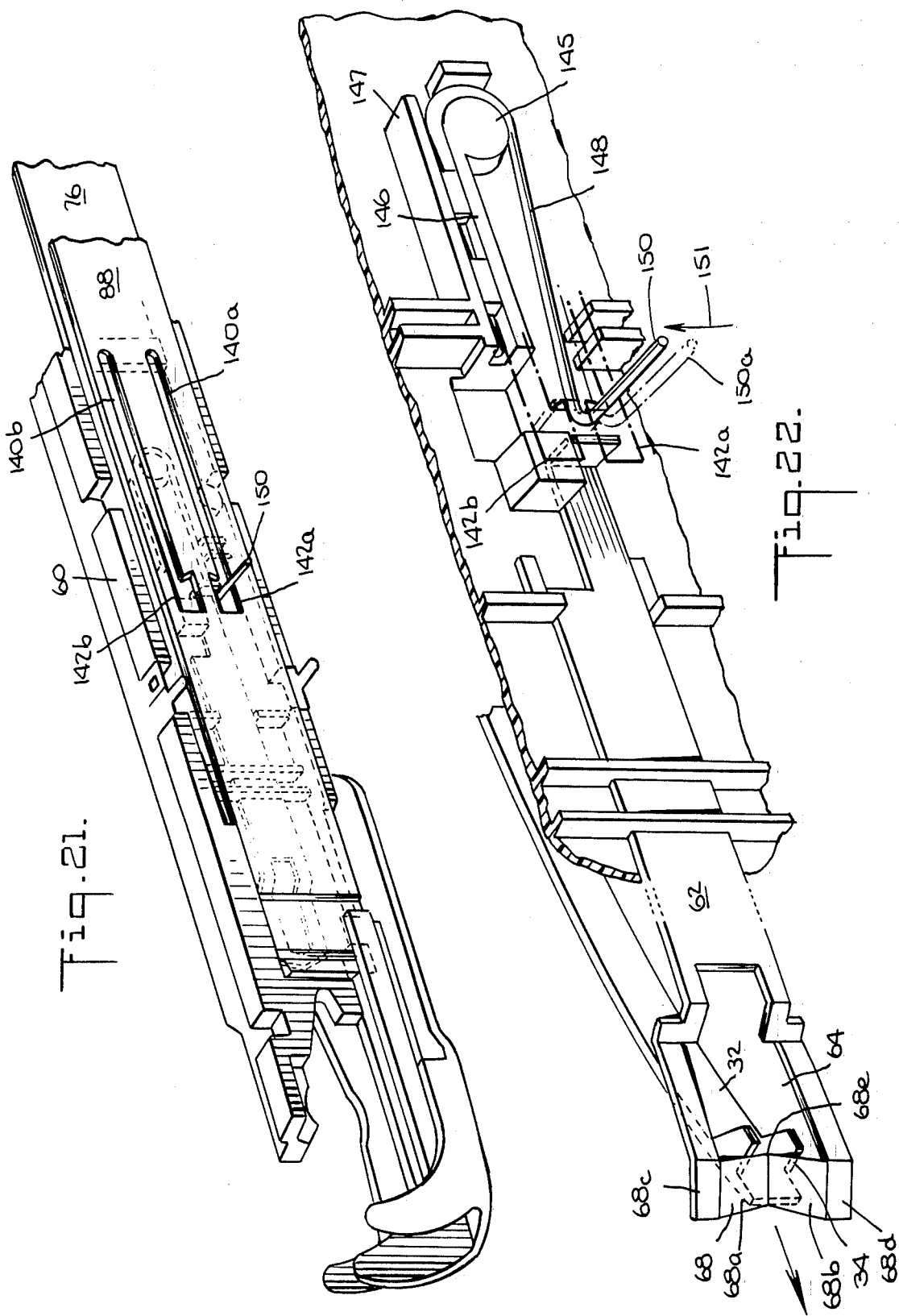

SURGICAL LIGATION AND CUTTING DEVICE WITH SAFETY MEANS

BACKGROUND OF THE INVENTION

This invention relates to surgical apparatus. More particularly, this invention relates to safety apparatus for surgical instruments which ligate and cut body tissue.

The tissue is ligated by two plastic clips ejected from a clip cartridge by pushers and compressed by an anvil at spaced locations about the tissue. The ligated tissue then is cut between the clips by a knife. The safety apparatus prevents operation of the instrument when there are no clips presented to the pushers which can be ejected from the instrument. The safety apparatus also includes a means to alert the surgeon that the pusher has jammed on its return stroke at the completion of a ligating and cutting operation.

Several safety devices have been proposed for surgical instruments which use metal staples or clips. U.S. Pat. No. 3,545,444 describes a suturing and cutting instrument which applies a pair of wire sutures to a tubular tissue structure inserted into an anvil assembly. The wire sutures are ejected from a cylindrical carriage assembly by a pusher. As they are ejected, the sutures are wrapped about the tubular structure by an anvil bending surface to ligate the tubular structure. When suturing is complete, the pusher advances a knife, which severs the tubular structure between the sutures. When the carriage assembly is empty, a locking spring blocks forward movement of the pusher.

U.S. Pat. No. 3,844,289 relates to a staple carrying hemostat. A surgeon clamps a bleeder by closing the jaws of the hemostat about the bleeder. The surgeon next activates a staple pusher in a staple cartridge to apply a U-shaped metal staple to the bleeder to stop the flow of blood. If the staple cartridge is empty or the staples become jammed, a spring stop blocks the staple pusher and prevents operation of the device.

U.S. Pat. No. 3,955,581 relates to a surgical instrument which ligates, sutures and divides organic tubular structures. It operates in three stages to enclose the tubular structure within the jaws of a staple cartridge, crimp the tubular structure with a pair of metal staples advanced from the cartridge by a pusher and divide the tubular structure with a knife blade advanced between the two staples. A clutch prevents retraction of the pusher and knife until the tubular structure is completely ligated, sutured and divided.

U.S. Pat. No. 4,086,926 shows a three stage device which includes a spring having a projection blocking the clip pusher when the staple cartridge is empty.

For certain surgical procedures, ligatures in the form of fasteners or clips of X-ray transparent plastic materials may be preferable to X-ray opaque metal staples. In addition to X-ray transparency, clips of plastic material also have the advantage that they can be made biologically absorbable.

Clips of plastic material cannot be substituted for metal staples in prior ligating and dividing instruments because plastic clips cannot be closed by clinching or crimping in the way that metal staples are clinched or crimped. Unlike metal staples, plastic clips will not hold a shape to which they are deformed unless parts of the clip mechanically interlock with one another. Thus, the means employed in prior ligating and dividing instruments for clinching or crimping metal staples around the tissue are not suitable for use with plastic clips.

The problems of storing and feeding plastic clips also are different from those associated with metal staples. Specifically, plastic clips must be arranged in a clip train with each clip attached to a preceding clip in the train. This allows the forwardmost clip in the clip train to be advanced by a clip pusher into position for ligating tissue structures. Because they are connected to the forward clip, the preceding clips in the clip train also are advanced. At the completion of the ligating operation, the clip pusher returns behind the next clip in the train ready for another ligating operation. The shape of plastic clips and their arrangement in a clip train require a pusher which is relatively small and delicate. The safety devices developed for prior instruments using metal staples or clips are unsuitable for a device using plastic clips because the pusher may be bent if it were blocked. Bending of the pusher would allow the knife to be advanced despite the blockage of the pusher. If the instruments were operated under these conditions, unligated tissue would be severed and injury to the patient might result.

SUMMARY OF THE INVENTION

It is an object of the invention to provide safety apparatus for a surgical instrument which ligates and cuts body tissue.

It is a further object of the invention to provide such a safety apparatus for a surgical ligating and cutting instrument which uses plastic clips for ligation.

Another object of the invention is to provide a safety apparatus for a surgical ligating and cutting instrument which prevents advancement of the knife in the event a clip pusher in the instrument is not presented with a clip for ligating tissue to be cut.

Another object of the invention is to provide a safety mechanism for a surgical ligating and cutting instrument which prevents release of tissue from the instrument if the clip pusher jams and does not return to its initial position at the completion of a ligating and cutting operation.

In accordance with these objects, a safety mechanism for a surgical instrument which ligates body tissue at spaced apart locations and then divides the tissue between the ligations is disclosed. The instrument has two spaced apart channels, each containing a plastic clip train. A clip pusher associated with each of the channels advances the clips along the channels and into a pair of jaws restraining a tissue structure inserted into the instrument. The instrument applies the clips at two spaced apart locations on the tissue to effect ligation. A knife between the two channels divides the ligated tissue structure between the spaced apart clips. An actuating and sequencing mechanism is connected to the pusher and the knife. If no clip were present for advancement by the pusher when a surgeon actuates the instrument, for example, because the channel is empty or because the clip train has broken, the pusher would enter a slot and advance a safety mechanism until a blocking means engages an opening in the portion of the sequencing mechanism advancing the knife. This directly blocks the knife and prevents cutting of unligated tissue. The surgical instrument also is provided with a latch which prevents the release of tissue from the jaws when the pusher jams and fails to return to its initial position.

BRIEF DESCRIPTION OF THE DRAWINGS

FIG. 2 is an exploded, perspective view of a portion of the cartridge and handle of FIG. 1.

FIG. 2D is a detailed sectional view showing the operation of the anti-jamming mechanism of FIG. 2.

FIG. 3 is an exploded, perspective view of a portion of the cartridge of the FIG. 1 instrument.

FIG. 4 is an exploded, perspective view of a portion of FIG. 3.

FIG. 5 is a broken, sectional view of the FIG. 1 instrument showing the actuating and sequencing mechanism.

FIG. 7 is a side sectional view of a portion of the FIG. 1 surgical instrument showing the condition of the jaws and tissue restraining mechanism when a tubular tissue structure is inserted into the instrument.

FIG. 8 is a side sectional view similar to FIG. 7 showing advancement of the jaws towards the tissue restraining mechanism to hold a tubular tissue structure in the instrument.

FIG. 9 is a top sectional view of the instrument taken along line 9—9 in FIG. 8.

FIGS. 10-12 are top sectional views similar to FIG. 9 sequentially illustrating the normal ligating and cutting operation of the surgical instrument of the present invention.

FIGS. 13 and 14 are top sectional views, similar to FIG. 9, sequentially illustrating the operation of the safety mechanism.

FIG. 15 is a broken, side sectional view of a portion of the FIG. 1 surgical instrument showing the latch mechanism of the invention when the instrument is in its initial position.

FIGS. 16 and 17 are sectional views of the FIG. 15 latch mechanism showing the latch disengaged and engaged, respectively, as the tissue is being restrained in the jaws of the instrument.

FIG. 18 is a broken sectional view, similar to FIG. 15, showing the condition of the latch mechanism in the event the pusher mechanism is jammed in returning to its initial position at the completion of a ligating and cutting operation.

FIG. 19 is an exploded view of a portion of a surgical instrument having an alternative safety in accordance with the invention.

FIG. 20 is an exploded view of a portion of FIG. 19.

FIG. 21 is a detailed view of the exploded elements of FIG. 19 after assembly.

FIG. 22 is a detailed perspective view showing the operation of the alternative safety.

DETAILED DESCRIPTION OF THE INVENTION

Figure 1:
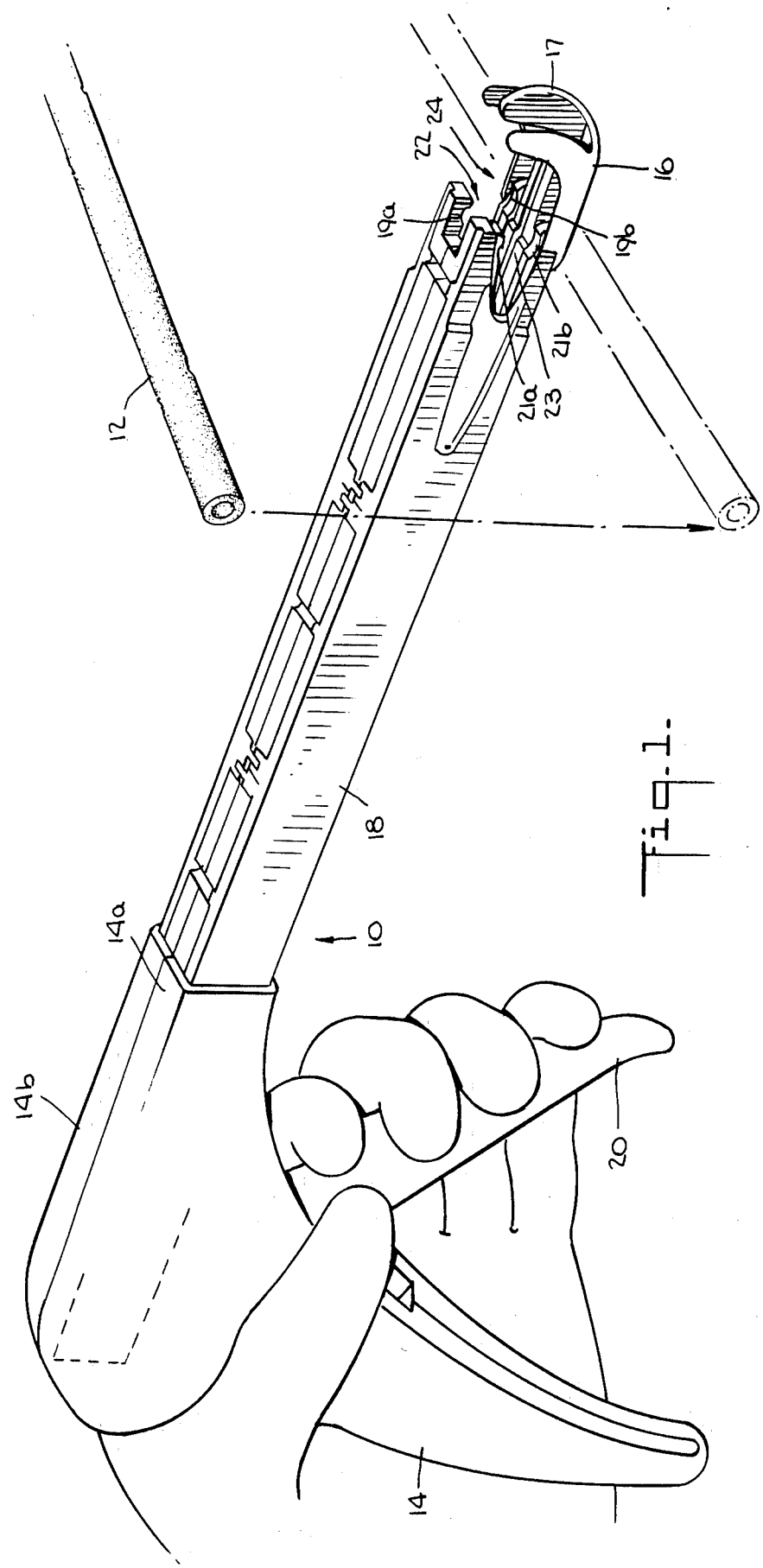
FIG. 1 is a perspective view of a surgical instrument in accordance with the present invention.

Throughout this detailed description of the invention, like elements are given like reference numerals in all of the Figures.

FIG. 1 shows a surgical instrument 10 which grasps an organic tissue structure, such as a tubular tissue structure 12, ligates the tissue structure by applying two plastic clips at spaced locations on the tissue structure and severs the tissue structure between the clips. The surgical instrument comprises a handle 14 at the proximal end of the instrument, a restraining mechanism 16 at the distal end of the instrument and a cartridge 18 between the proximal and distal ends of the instrument.

A trigger 20 protrudes from the handle. It is connected to an actuating and sequencing mechanism inside the handle and cartridge which properly sequences the surgical operations performed by the instrument when a surgeon squeezes the trigger and handle together.

The cartridge 18 is slidable with respect to the handle 14 and includes a pair of channels each housing a train of plastic clips. These clips are advanced by a pusher towards anvil surfaces in jaws 19a, 19b, 21a and 21b fixed to the distal end of the cartridge 18. This closes the clips and ligates tissue placed into the instrument. A knife is then advanced between the channels and the clips and severs the ligated tissue.

The restraining mechanism 16 is stationary during the initial stages of the instruments's operation and confines the tissue placed in the instrument to V-shaped recesses 22 and 23 between the jaws when the cartridge is advanced towards the restraining mechanism. The restraining mechanism is slidable away from the handle and the cartridge at the end of the instrument's operation to facilitate ejection of clips from the channels while effectively restraining the tissue until the surgeon is ready to release the trigger.

The surgical instrument of FIG. 1 operates as follows. It is shown in its initial position in FIG. 1. An organic tissue structure, which can be a tubular tissue structure 12, such as a vein, artery, umbilical cord, intestine or the like, is inserted by the surgeon into space 24 between the distal end of the cartridge 18 and the restraining mechanism 16. The surgeon then grasps the handle 14 and trigger 20 and squeezes them together. During the initial stage of operation, the cartridge 18 advances distally with respect to the handle 14 and towards the stationary restraining mechanism 16. This confines the tissue to V-shaped recesses 22 and 23 but does not close or damage the tissue. During the next stage of operation, the cartridge stops moving but clips are advanced from a pair of clip trains in the cartridge by clip pushers toward the V-shaped recesses and around the tissue at two spaced apart locations. As the clips are advanced, the ends of each clip are cammed closed by anvil surfaces in jaws 19a, 19b, 21a and 21b, thereby ligating the tissue inserted into the instrument. As the surgeon continues to squeeze the trigger and handle, a knife advances in a distal direction between the two clip channels. As the knife approaches the ligated tissue, the restraining mechanism advances in a distal direction far enough to permit ejection of the clips from the cartridge, but not far enough to permit release of the tissue from the V-shaped recesses. The knife, however, advances faster than the restraining mechanism and eventually severs the ligated tissue between the clips against a knife anvil 17. The operation of the instrument is now complete. When the surgeon releases the trigger, the knife and the restraining mechanism retract, the clip pushers retract behind the next clips in the clip trains and the cartridge retracts into the handle portion of the instrument. The instrument is now back to its original starting position ready for another ligating and cutting operation.

FIGS. 2 through 4 show exploded views of a portion of the FIG. 1 surgical instrument on one side of the instrument's vertical plane of symmetry. Taken together, they represent the complete restraining mechanism and half 14a of the handle 14 and cartridge 18 on one side of such vertical plane of symmetry. The remaining portion of the cartridge on the other side of this plane of symmetry is a mirror image of the FIGS. 2 through 4 structure with the exception of structure associated with the knife and the restraining mechanism, to be described later. Likewise, the other half 14b of the handle 14 (FIG. 1) is a mirror image of the half 14a shown in FIG. 2.

In addition to half 14a of handle 14, FIG. 2 shows a clip storage assembly 26 of cartridge 18. The clip storage assembly includes a wrap housing 27, clip pusher bar 30, clip track cover 40, clip train 42, clip positioning pawl 58, clip track 60 and safety 62.

Wrap housing 27 is a thin metal cover for one side of the cartridge 18. Tabs 28 on the housing interlock with similar tabs on a mirror image wrap housing covering the other side of the cartridge, as shown in FIG. 1, to hold the elements of the cartridge together. A dimple 29 is formed near the distal end of the wrap housing to provide space for the clip pusher 32 when the clip pusher projection 34 passes over the forward most clip on the return stroke, an arrangement shown more clearly, for example, in FIG. 10.

The clip pusher bar 30 is a thin metal slide which slides in the channel formed by the wrap housing 27, clip track cover 40, and clip track 60. At the distal end of the pusher bar is a clip pusher 32 and a projection 34 which extends through slot 41 in the clip track cover 40. When the instrument is operated, the projection 34 lodges itself behind the apex 50 of the forwardmost clip in the clip train 42. The clip pusher advances this clip as the pusher bar is urged forwardly. The clip pusher 32 is resilient so that, as it engages the forwardmost clip in the clip train, it exerts a biasing force on the clip against clip track 60 in the direction of the instrument's vertical plane of symmetry.

The clip track cover 40 is formed of metal and separates the pusher bar 30 from the clip train 42. It confines clip train 42 to a channel formed in the rear side of clip track 60.

Clip train 42 has a series of interlocked plastic clips 43. Each clip is triangular and has two spaced arms 44 joined at apex 50. The ends of the clips have interlocking elements 48 which maintain the clip closed when the arms of the clip are cammed closed by advancement of the clip against anvil surfaces formed in the jaws 21a and 21b. Tabs 46 on each clip engage the interlocking elements 48 of the preceding clip in the train. This allows the clip pusher 32 to advance the whole clip train when it pushes the apex 50 of the forwardmost clip. When the pusher advances this clip against the anvil surfaces and the arms of the clip are closed, the clip is disengaged from the next clip in the clip train and ejected from the instrument. The next clip in the clip train has now been advanced to the initial position of the just ejected clip. When the surgeon releases the instrument, the pusher returns behind this next clip. As shown more clearly in FIGS. 8–11, clip positioning pawl 58 is situated so that it prevents the new forwardmost clip from being retracted as the pusher returns behind it.

Figure 2A:
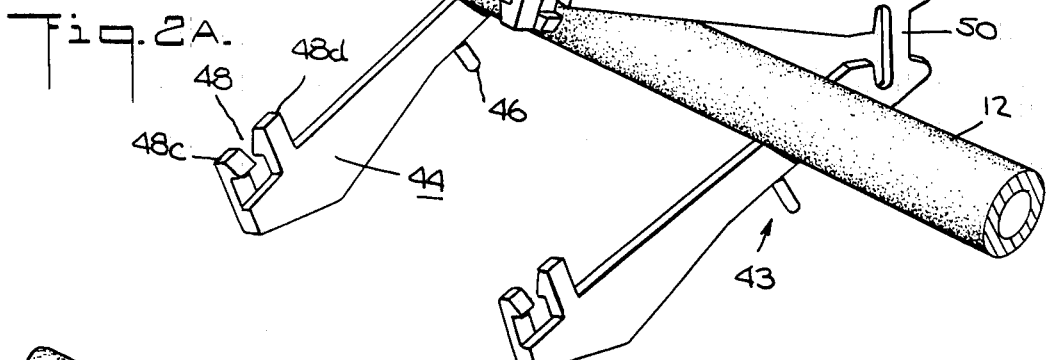
FIGS. 2A, 2B and 2C show in detail the closing of the plastic clips about tissue inserted in the instrument.
Figure 2B:
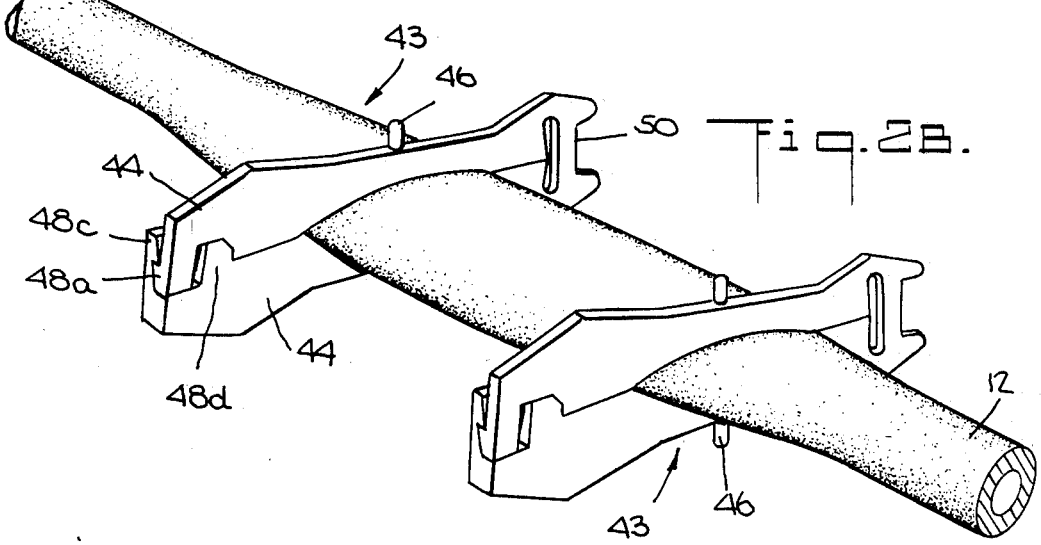
Figure 2C:
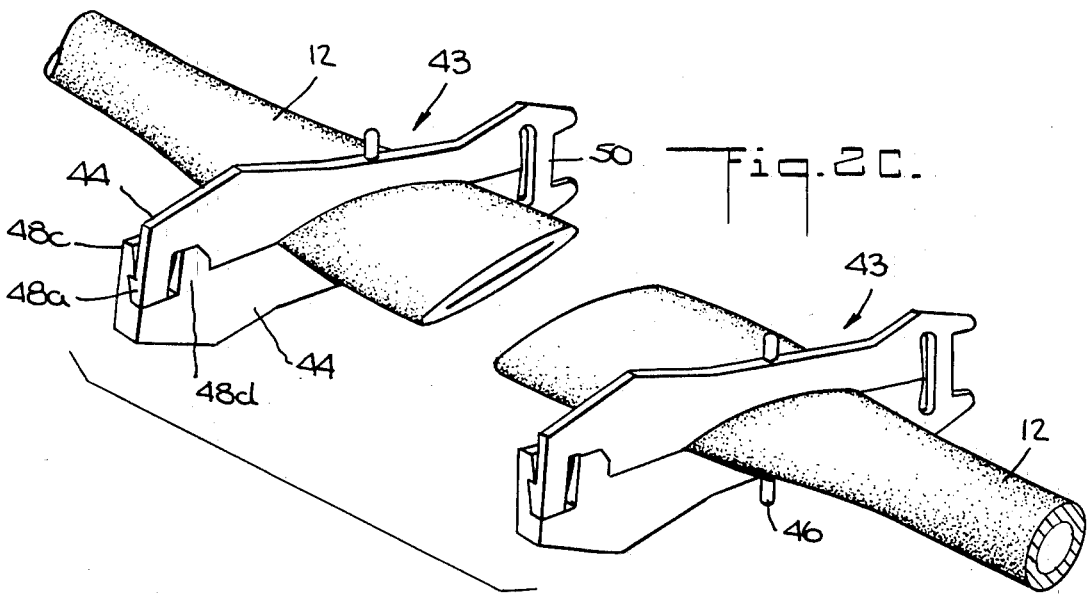

FIGS. 2A, 2B and 2C show, in detail, clip closure, tissue ligation and tissue cutting, respectively. The clips are held in a closed position to ligate tissue 12 by the interlocking of elements 48a and 48b on one arm of the clip with elements 48c and 48d on the other arm of the clip.

The rearmost clip of the clip train is seated in a U-shaped clip holder 52 which prevents this clip from becoming skewed when all of the clips ahead of it have been ejected from the instrument. The clip holder is biased forwardly by spring 54 which is compressed between the clip holder 52 and spring holder 56. The spring forces the clip train forwardly only until the first few clips have been ejected from the instrument. After that, the spring is completely relaxed and has no effect.

Clips 43 in the preferred embodiment are made from a biologically absorbable copolymer which is a polyester derivative of lactide and glycolide. Such material is absorbable by the body and is radiotransparent. Of course, any plastic material which can be formed into suitable clips, regardless of whether it is absorbable by the body, can be used. Such material may be, for example, polyester polyamid, and the like.

Clip track 60 is formed of plastic material, such as LEXAN polymer manufactured by the General Electric Company, and contains a channel on its rearward side, as viewed from FIGS. 2 through 4, in which the clip train 42 is located. The forward side of the clip track 60 forms a channel for a safety 62 comprised of thin, resilient metal having an opening 64, a lip 68 and a blocking spring 66. As will be described in connection with FIGS. 3 and 4, the forward side of the clip track also forms a channel for the restraining mechanism pusher bar and the knife pusher bar.

An anti-jamming mechanism comprises a ratchet 31 formed on clip pusher 30 operating in conjunction with pawl 69 on clip track 60 through a slot 45 in cover plate 40. This anti-jamming mechanism is provided to prevent an additional clip from being advanced from the instrument until the forwardmost clip has been completely closed and ejected from the instrument when it is operated. FIG. 2D shows in detail the interaction of the proximal end of ratchet 31 with the proximal end of pawl 69. When an operating cycle begins, ratchet 31 is located relative to pawl 69 as shown in FIG. 2D at reference numeral 31a. When clip pusher bar 30 begins to advance relative to clip track 60, ratchet 31 moves to position 31b in FIG. 2D shortly after the distal end of clip pusher 32 moves distally past the distal end of pawl 58. In position 31b, latch surface 33 on one side of pawl 69 prevents ratchet 31 and clip pusher bar 30 from retracting in a proximal direction, even if trigger 20 is prematurely released. This prevents clip pusher 32 from retracting to a position behind pawl 58 and picking up another clip until after the clip which pusher 32 has already begun to advance has been completely closed and ejected from the instrument.

As clip pusher 32 is ejecting a completely closed clip from the jaws, ratchet 31 passes around the distal end of pawl 69, as shown at position 31c in FIG. 2D. When trigger 20 is released following ejection of the closed clip, ratchet traverses the opposite side of pawl 69 as shown in part by the reference number 31d in FIG. 2D and returns to its initial position 31a as the remainder of the instrument returns to its initial condition. From the foregoing, it will be seen that anti-jamming mechanism prevents double feeding of clips, which could cause the apparatus to malfunction and jam.

FIG. 4 shows the placement of safety 62 within the channel formed by clip track 60. FIGS. 3 and 4 show the placement of a thin, metallic restraining mechanism pusher bar 76 next to the safety. Slot 78 on the pusher 76 is oriented such that blocking spring 66 protrudes through it. Cutout 80 at the distal end of pusher 76 cooperates with tab 86 on the restraining mechanism to rigidly connect the restraining mechanism with pusher bar 76.

Both pusher bar 76 and safety 62 are slidable with respect to the clip track 60. The proximal end of pusher bar 76 has a tab 83 which cooperates with distal and proximal end stops 114 and 116 in handle 14 (FIG. 5) to limit the longitudinal travel of the restraining mechanism between fixed points. A spring 84 is connected between an eyelet 82 on pusher bar 76 and a post 85 in the handle so as to bias the pusher bar 76 and the restraining mechanism 16 towards proximal end stop 116. The proximal end of pusher bar 76 also has a ramp 77 which engages a pin 104 connected to the trigger which advances pusher bar 76 towards the distal end of the instrument when the trigger is squeezed.

FIGS. 3 and 4 also show the connection of the clip pusher bar to the proximal end of the clip track 60. A spring 70 is connected between eyelet 36 on the pusher bar and eyelet 72 formed in metal insert 74 affixed to the proximal end of clip track 60. The spring 70 biases the clip pusher bar towards the proximal end of clip track 60 and cartridge 18.

FIG. 3 shows the manner in which the cutting mechanism is fitted into the clip track 60 over the restraining mechanism pusher bar 76. The cutting mechanism comprises a thin, metallic knife pusher bar 88 with a knife 90 attached to its distal end. The pusher bar 88 has an opening 92 which cooperates with blocking spring 66 when safety 62 has been slid forwardly by the clip pusher 32. An eyelet 94 at the proximal end of pusher bar 88 is connected to one end of a spring 96. The other end of spring 96 is connected to an eyelet 98 on insert 74. Spring 96 biases the knife pusher bar towards the proximal end of the clip track 60 and cartridge 18. The proximal end of the knife pusher bar has a ramp 97 which cooperates with a camming surface 106 connected to the trigger which urges the knife pusher bar 88 and knife 90 towards the distal end of the instrument when the trigger is squeezed.

As described earlier, the projection 34 on clip pusher 32 is lodged behind apex 50 of the forwardmost clip when the instrument is operated. When the pusher engages the forwardmost clip, it biases the clip against the clip track 60. If no clip were present, the bias of the pusher would cause the pusher to project through slot 41 in the cover plate 40, slot 61 in clip track 60 and opening 64 in safety 62. Advancement of the clip pusher 32 would cause the projection 34 to engage lip 64 and slide the safety 62 forwardly until blocking spring 66 entered the opening 92 on the knife pusher bar 88. Blocking spring 66 in conjunction with abutment 63 (FIG. 13) would prevent forward movement of the knife if no clip were present for engagement with pusher 32.

The assembled cartridge 18 fits into a channel 19 in the handle 14, shown in FIG. 2. The proximal end 65 of the clip track 60 slides within channel 19 between end stops 13 and 15. As will be explained in connection with FIGS. 5 and 6, the trigger is connected to the clip pusher bar 30. The trigger is spring biased so that the clip pusher bar 30 and cartridge 18 are urged towards the proximal end of the instrument. The cartridge 18 slides forwardly with respect to a stationary restraining mechanism pusher bar 76 when the trigger urges the clip pusher bar forwardly during the initial squeezing operation of the instrument. This movement encloses tissue inserted in the instrument within the tissue restraining mechanism and jaws and continues until abutment 67 on the clip track reaches end stop 15 in the handle.

FIG. 5 shows the arrangement of the trigger in the handle and its relationship with a portion of an actuating and sequencing mechanism on one side of the instrument's vertical plane of symmetry. FIG. 5 represents the initial position of the surgical device before the surgeon squeezes the trigger. Trigger 20 is a molded plastic sleeve shaped into the form of a hand grip on one arm of a metal lever 100 pivoted about a post 102. The other arm of the lever has a post 104 which extends through slot 38 in the clip pusher bar 30. The post 104 cooperates with slot 38 to advance the clip pusher bar 30 and the clip pusher 32 in a distal direction when the trigger 20 is squeezed. The post 104 also contacts the ramp 77 on restraining mechanism pusher bar 76 to advance pusher bar 76 and restraining mechanism 16 at the end of the instrument's operational cycle. The other arm of the lever also has a camming surface 106. This camming surface contacts ramp 97 of the knife pusher bar 88 to advance the knife pusher bar 88 and the knife 90 towards the distal end of the instrument. A spring 107 connected between eyelet 108 on the lever 100 and post 110 in the handle biases the lever and the trigger in a clockwise direction, as viewed in FIG. 5. The cartridge 18 and the clip pusher bar 30 are thus maintained in their proximal-most positions in the handle before the trigger is squeezed.

Spring 96 biases the knife pusher bar 88 in a proximal direction so that tab 93 is urged against stop 113. Stop 113 is a tab formed on the mirror image clip track shown in FIG. 1 but not shown in FIGS. 2 through 6. The stop 113 fits into recess 113a on the clip track 60 shown in FIGS. 2 through 6. Spring 94 urges the restraining mechanism pusher bar 76 in a proximal direction so that tab 83 is urged against end stop 116. It can be seen in FIG. 5 that tab 83 limits the movement of the pusher bar 76 between end stops 114 and 116.

Figure 6:
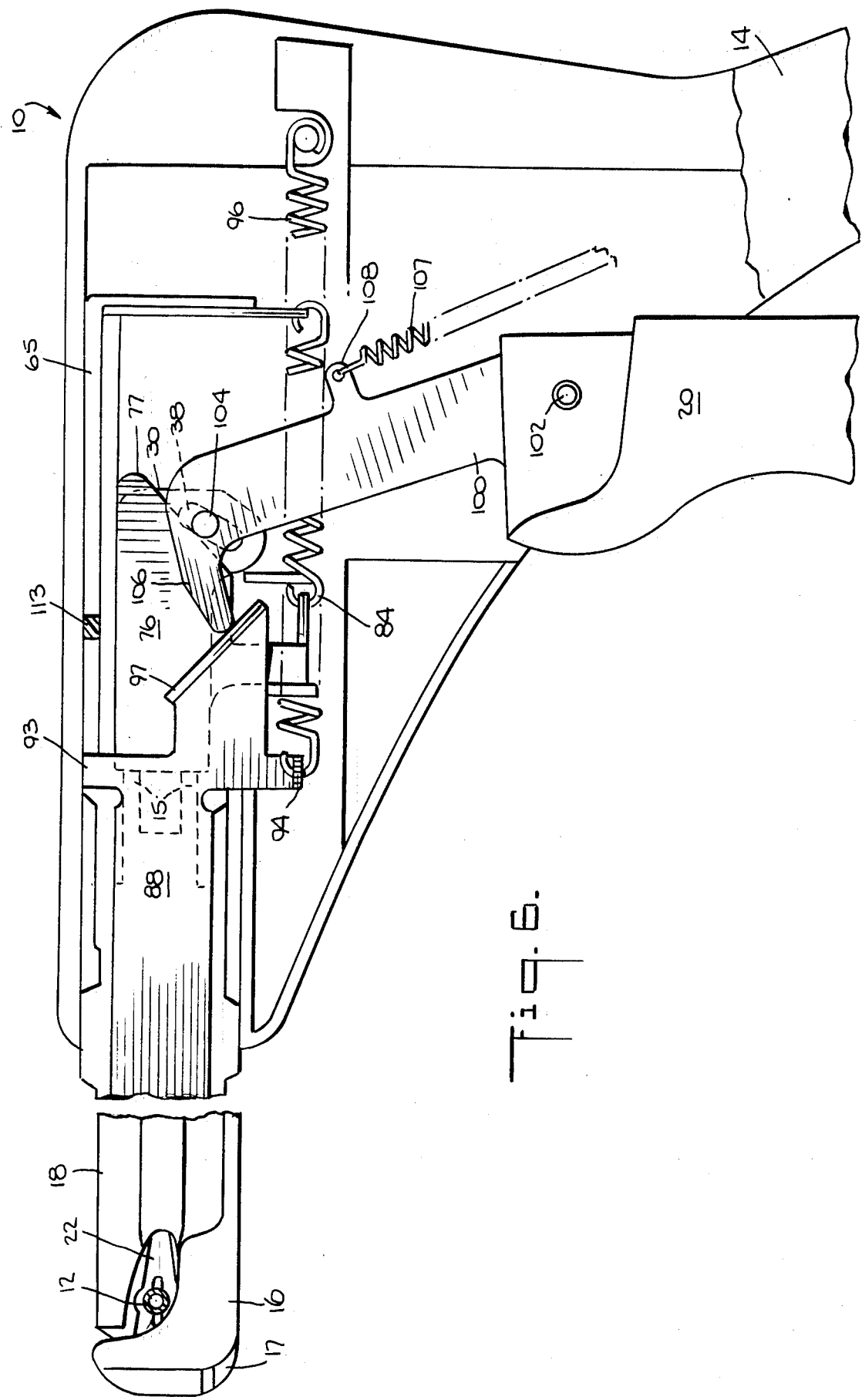
FIG. 6 is a broken, sectional view, similar to FIG. 5, showing the condition of the actuating and sequencing mechanism between the ligating and cutting operation.

FIG. 6 illustrates the operation taking place inside the handle of the surgical instrument when the surgeon squeezes the trigger. As the surgeon squeezes the trigger, the lever 100 pivots in a counterclockwise direction about post 102. Pin 104 slides upwardly in slot 38 in the pusher bar 30 and urges pusher bar 30 towards the distal end of the instrument. The spring constant of spring 70 is such that, when the lever 100 urges the pusher bar 30 towards the distal end of the instrument, the clip track 60 and cartridge 18 are advanced in tandem with the clip pusher bar. Due to the abutment of tab 93 against stop 113, the knife pusher bar 88 also is advanced with the clip pusher bar and the clip track.

This distal motion of the clip pusher bar, clip track and knife pusher bar continues until the abutment 67 on the clip track engages stop 15 in the handle. The clip track is then restrained from further motion but the clip pusher bar continues to be advanced, now against the bias of spring 70. The clip pusher 32 at this time begins to advance the forwardmost most clip from the clip train. Somewhat later cam surface 106 contacts ramp 97 of knife pusher bar 88 and begins to advance bar 88 with respect to the clip track 60. Thus, clips are fed to the jaws to be applied about the tissue inserted in the instrument and then a knife cuts the tissue after the clips have ligated the tissue. Before the knife cuts the tissue, pin 104 contacts ramp 77 on restraining mechanism pusher bar 76. Until this time, bar 76 and the restraining mechanism 16 have been stationary with respect to the handle 14 and the cartridge 18. Movement of pin 104 against ramp 77 advances the restraining mechanism 16 a short distance away from the jaws to aid the ejection of the clips from the cartridge. However, this distance is not enough to release the tissue from the jaws. As the restraining mechanism is advanced, the knife advances more rapidly and cuts the tissue against knife anvil 17. The surgeon then can release the trigger which releases the ligated and severed tissue from the instrument. The springs thus far described return the instrument to the position shown in FIG. 5 so that it is ready for another ligating and cutting operation.

FIGS. 7 and 8 show sequentially the operation at the distal end of the instrument which restrains the tissue to be ligated and cut. FIG. 7 shows the condition of the instrument before the surgeon squeezes the trigger and as the tissue 12 is inserted into the instrument. FIG. 8 shows the confinement of tissue 12 between jaws 19a and 19b within recess 22. This confinement is achieved by movement of cartridge 18 forwardly toward the restraining mechanism 16.

FIGS. 7 and 8 also show the clip train 42 within channel 118 in the clip track 60. The clips are confined within channel 118 by coverplate 40 (FIG. 2). The channel terminates at its distal end in a pair of anvil surfaces 120 and 121 which close the forwardmost clip in the clip train as it is advanced by clip pusher 32. When the clip is completely closed, it ligates a tubular tissue structure 12 inserted into the instrument.

FIGS. 9 through 12 demonstrate the ligating and cutting operation at the distal end of the surgical instrument. They also clearly show the arrangement of mirror image elements on each side of the instrument's vertical plane of symmetry.

FIG. 9 shows the instrument after the tissue 12 has been restrained by movement of cartridge 18 and jaws 19a, 19b, 21a and 21b towards the restraining mechanism 16. The apex 50 of the forwardmost clip, is located just ahead of the clip positioning pawl 58 which prevents retraction of the forwardmost clip, and thus the entire clip train, back towards the proximal end of the instrument. Projection 34 of clip pusher 32 is located behind the clip positioning pawl between the apexes of the forwardmost clip and the next clip in the clip train.

FIG. 10 shows the initial advancement of the clip pusher with respect to the clip track after the tissue has been restrained. It has advanced from its position behind the clip positioning pawl and has forced the pawl into opening 64 in safety 62. The corner formed by projection 34 and the distal end of the clip pusher has engaged the apex of the forwardmost clip and has begun to push it forward. The shape of the clip pusher with respect to apex 50 thus prevents the clip pusher from entering the opening 64 in safety 62.

FIG. 11 shows the condition of the instrument after further advancement of the clip pusher. The clip pusher has advanced the clip against the anvil surfaces which have closed the clip ligating the tissue. The knife has advanced, but has not cut the tissue.

Figure 12:
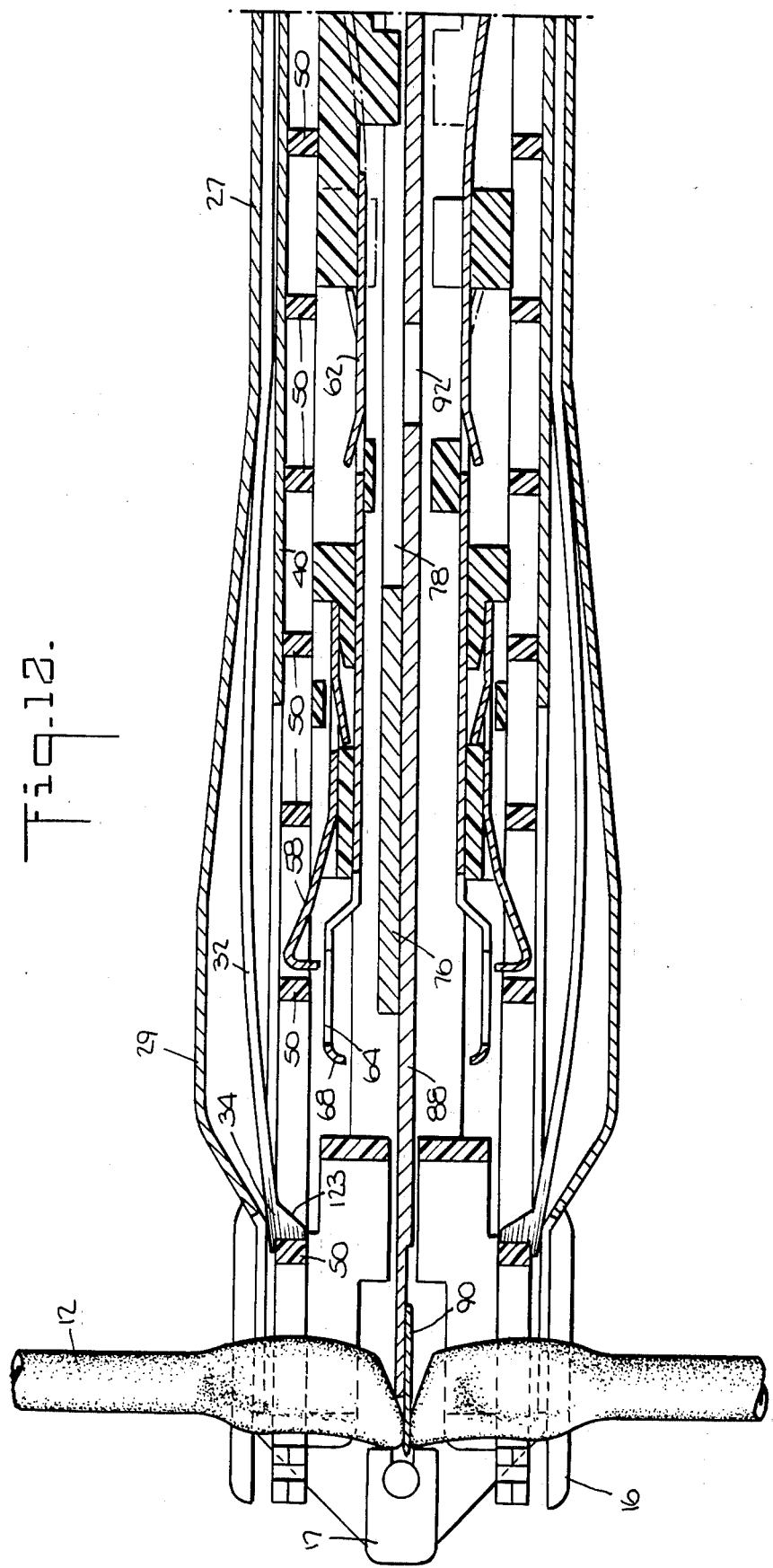

FIG. 12 shows the instrument cutting the tissue. The restraining mechanism has advanced with respect to the jaws and the clip has been ejected from the cartridge. The knife has advanced against the knife anvil to cut the tissue. When the surgeon releases the trigger, the ligated and cut tissue is released from the instrument.

Release of the trigger returns the knife to the position of FIG. 10. The clip pusher is also returned to its FIG. 10 position after having been cammed over the new forwardmost clip in the clip train. This camming operation is achieved by retraction of camming surface 123 against the clip apex 50. The clip is held stationary by the clip positioning pawl 58, while the projection 34 on the clip pusher rides over the clip. When the clip pusher has returned to its FIG. 10 position, then the cartridge 18 retracts into the handle and away from the restraining mechanism.

FIG. 13 shows a point in the operation of the surgical instrument somewhat later than that shown in FIG. 10. FIG. 13 differs from FIG. 10 in that a clip is not present in the forwardmost position in the clip train on the distal side of the clip positioning pawl 58. Such a situation can occur, for example, if the clip train separates, or if the last clip in the clip train has been used. It also can occur if one of the clips becomes skewed in the cartridge such that it cannot be engaged properly by the clip pusher. FIG. 13 shows that the projection 34 on the clip pusher enters opening 64 in safety 62 when the clip pusher is advanced over the clip positioning pawl 58. Further advancement of the clip pusher first causes projection 34 to engage lip 68 on the safety and then causes the clip pusher to slide safety 62 forwardly. This causes blocking spring 66 to enter opening 92 in the knife pusher bar 88. Advancement of the knife pusher bar 88 urges blocking spring 66 against an abutment 63 formed in the clip track associated with the mirror image portion of the instrument not being described here in connection with FIGS. 9-14. The knife pusher bar 88 thus is effectively prevented from advancing by the blocking spring 66 sheared between pusher bar 88 and the abutment 63. This prevents the severing of tissue left unligated by the absence or misalignment of the forwardmost clip in the clip train.

This arrangement is more effective for devices using plastic clips than those found satisfactory for devices using metal clips. As the pushers for plastic clips are less robust than the pushers for metal clips, it is possible that the pusher for plastic clips can be buckled against a blocking element placed in the path of the pusher, thus allowing the knife to advance and cut tissue. In this arrangement, however, the path over which the knife operates is directly blocked by spring 66. Also, in this arrangements, it is particularly difficult to overcome the blocking effect of the spring 66 because the spring must be sheared in order to advance the knife once the safety is activated.

The safety arrangement might be defeated, however, if the clip pusher jams on the distal side of pawl 58 and does not return completely to its initial position after a ligating and cutting operation. This can happen if the clip pusher is bent during a previous ligating and cutting operation or the next clip in the clip train is skewed so that the camming surface 123 is misaligned with respect to the apex of the next clip and cannot raise the clip pusher over this apex as the instrument returns to its initial condition. This is illustrated in the left hand portion of FIG. 18. Also, this can happen if the distal most clip in the clip train were missing and the pusher were to hang up on lip 68 of safety 62 when returning to its initial position after a ligating and cutting operation. If the instrument were allowed to operate again, the clip pusher would not advance a clip to ligate the next tissue structure inserted in the instrument. The clip pusher projection 34 may not enter the opening 64 in safety 62 and the knife path would not be blocked, thus permitting the instrument to sever unligated tissue.

FIGS. 15 through 18 show a latch mechanism on one side of the instrument's vertical plane of symmetry which deals with the clip pusher's failure to return to its initial position at the completion of the instrument's operation. It should be noted that the latch mechanism is located on the side of the instrument's vertical plane of symmetry not previously described. Elements which are mirror images of those already described are given reference numerals like those given to elements already described. FIG. 15 shows the condition of the latch mechanism when the clip pusher and cartridge are fully retracted in the initial position of the instrument. FIG. 16 shows the latch mechanism when the cartridge has been advanced to restrain tissue inserted in the instrument but before the clip pusher has begun to advance a clip from the clip train. FIG. 17 shows the latch mechanism when the clip pusher begins to advance with respect to the clip track 60. FIG. 18 shows the condition of the latch in the event the clip pusher jams.

The latch mechanism comprises a lever 127 rotatable about a post 129 fixed in the proximal end of clip track 60 between the clip pusher bar 30 and handle 14b. Lever 127 is biased in a counterclockwise direction, when viewed in FIGS. 15 through 18, by a spring 131. Finger 133 at the proximal end of lever 127 is thus forced against the proximal end of clip pusher bar 30. When the cartridge 18 and clip track 60 are advanced with respect to the handle 14b in the beginning of a cycle of operation (FIG. 16), the clip pusher bar 30 and the lever 127 move forwardly in tandem with respect to handle 14b until tab 134 at the distal end of lever 127 coincides with hole 135 in the handle. The clip pusher then begins to advance with respect to the clip track 60 and the lever 127. This frees the lever to rotate tab 134 into hole 135 and locks the clip track 60 and cartridge 18 with respect to the handle 14 (FIG. 17). The operation of the instrument then proceeds as previously described.

When cutting and ligating are completed and the surgeon releases the trigger, the clip pusher bar 30 returns to its position shown in FIG. 16, cams the finger 133 on lever 127 and rotates the tab 134 out of hole 135 and thereby allows the clip track 60 and cartridge 18 to retract into the handle. If the clip pusher projection 34 were to hang up when returning to its initial position, as shown in FIG. 17, the tab 134 would remain in hole 135 and the cartridge and clip track would be prevented from retracting into the handle. The restraining mechanism 16 and jaws 19a, 19b, 21a and 21b would continue to hold the previously cut and ligated tissue in the instrument, even after the surgeon completely released his grip on the trigger.

This would alert the surgeon to the jammed clip pusher. To release the tissue in this situation, the surgeon must grasp the cartridge and the handle and force the cartridge into the handle. This releases tab 134 and the instrument then should be discarded.

The latch, therefore, provides the surgeon with a means for determining when the clip pusher jams and does not return behind the next clip in the clip train when he releases the trigger. It allows him to discard the instrument before it can be used again in a situation where the safety features of the instrument would be defeated and tissue would be ligated before it was severed.

FIGS. 19 through 24 depict another embodiment of the invention. Elements similar to those already described in connection with FIGS. 1 to 18 have been assigned like reference numerals.

The knife pusher bar 88 in this embodiment differs from the knife pusher bar in the previous embodiment in that the knife pusher bar has a pair of elongated slots 140a and 140b instead of opening 92. These slots are narrow over most of their length with wider openings 142a and 142b at their distal ends.

As in the previous embodiment, this embodiment is provided with a safety 62 having an opening 64. This safety differs from the previous safety in that it does not have a blocking spring at its distal end. Instead, it has a tab 152 which extends at generally a right angle to the instrument's plane of symmetry. When the safety is in its distal most position, the tab 152 engages a portion of hairpin 144.

Lip 68 in this embodiment differs from lip 68 in the previous embodiment in that lip 68 comprises concave (as viewed in FIG. 22) strips 68a and 68b connecting two ramp surfaces 68c and 68d on the safety 62. Strips 68a and 68b form an apex 68e which is presented to pusher 32 when the distal most clip is absent or skewed. The apex 68e normally extends upwardly between the arms 44 of the distal most clip and facilitates engagement of the clip pusher with lip 68. When the distal most clip is oriented properly, advancement of the clip against ramp surfaces 68c and 68d cams the apex out of the path of the clip pusher so that the safety is not actuated as the pusher moves past lip 68. Apex 68e is advantageous when the distal most clip is present but not oriented properly. In this situation, a portion of the clip may prevent the clip pusher projection 34 from engaging lip 68 if apex 68e were not present.

Hairpin 144 comprises a pair of metal arms 146 and 148 resiliently connected and wrapped around post 145. Arm 146 is fixed to clip track 60 in cradle 147. Arm 148 has an end portion 150 at its distal end which extends generally perpendicularly to the instrument's plane of symmetry through slot 78 on the restraining mechanism pusher bar 76 and through slot 140a. The resilience of hairpin 144 urges arm 148 towards arm 146.

Tab 152 is configured such that the arm 148 and end portion 150 bear against tab 152 and force arm 148 away from arm 146 when the safety is in its distal most position. This causes projection 150 to be forced downwardly into the narrow portion of slot 140a so that the knife pusher bar is free to advance a distance defined by the entire length of slot 140a. When a clip is available to be advanced by clip pusher 32, the safety 62 remains in its distal most position during the operation of the instrument. The projection 150 does not interfere with the operation of the knife pusher bar.

When a clip is missing from the distal most end of the clip train, the clip pusher 32 enters opening 64 in safety 62. Forward movement of the clip pusher then advances safety 62 as in the previous embodiment (FIG. 24). Advancement of safety 62 causes tab 152 to disengage from arm 148 and end portion 150. The resilient bias of hairpin 144 then causes arm 148 to close towards arm 146. Extension 150 moves into opening 142a in slot 140a which blocks the pusher bar 88 from moving distally and prevents the cutting of unligated tissue. Compare reference numerals 150 and 150a in FIG. 22; see also FIG. 23. In all other respects, this alternative embodiment operates in the same manner as the previously described embodiment.

Figure 23:
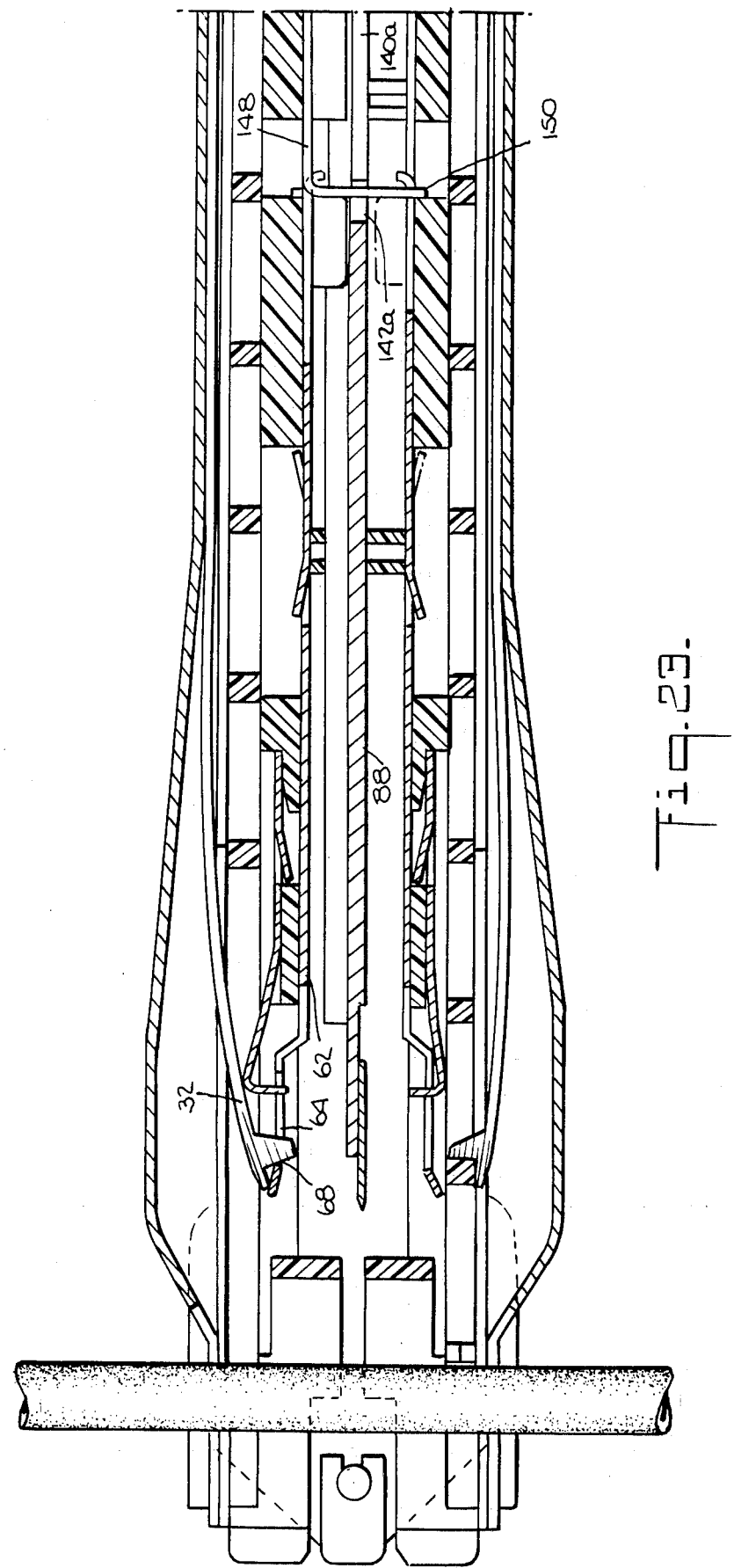
FIGS. 23 and 24 are top sectional views of the instrument showing sequentially the operation of the alternative safety.
Figure 24:
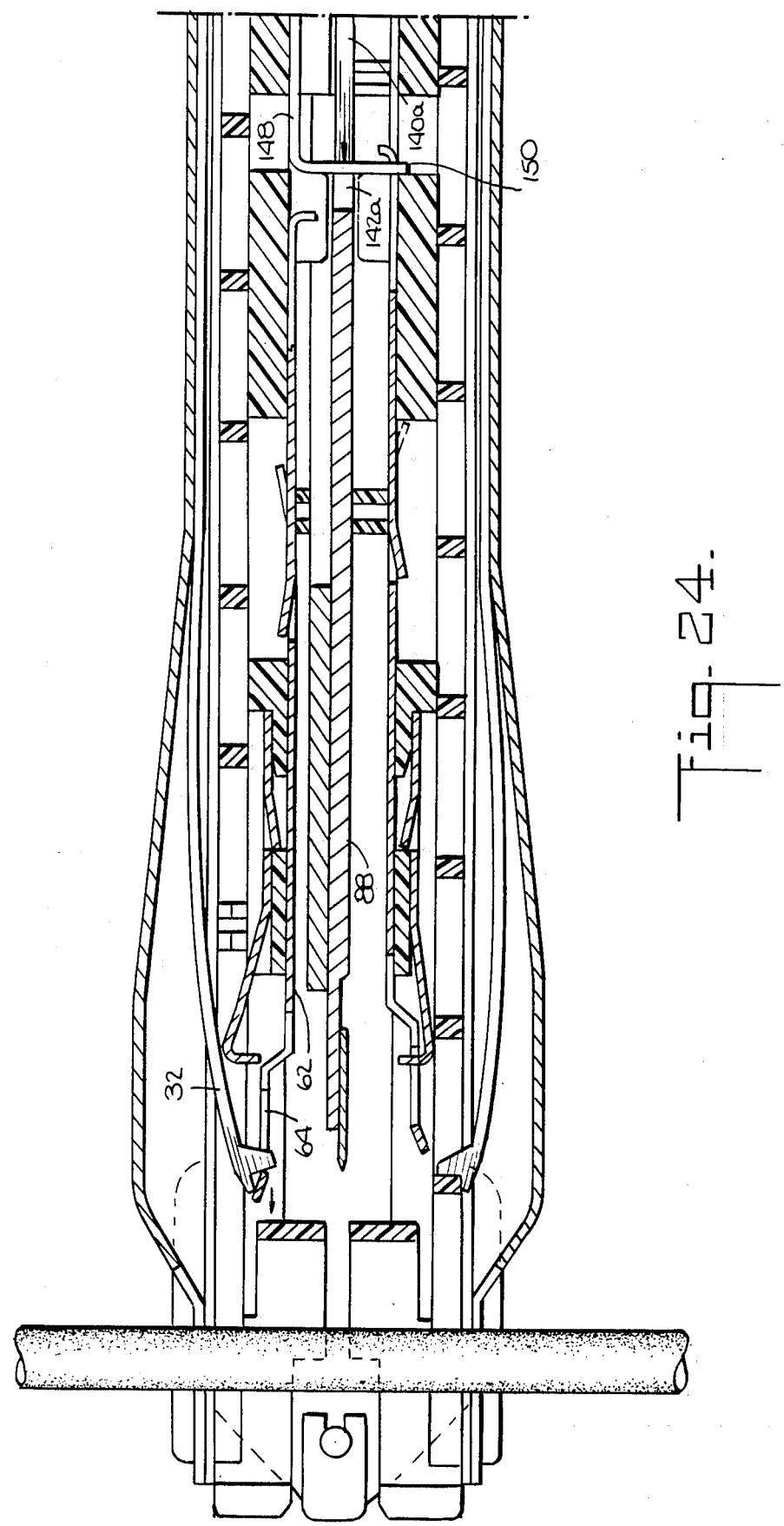

It will be apparent that the operation for only one channel has been described and that a mirror image safety is provided for the other channel of the instrument, as shown in FIGS. 23 and 24. This safety cooperates with slot 140b and opening 142b in the same manner as described above.

We claim:

1. An apparatus for ligating and cutting body tissue comprising:
   means for ligating body tissue at two spaced apart locations with two plastic clips separated from a pair of clip trains;
   means for cutting said body tissue between said spaced apart locations after said body tissue has been ligated by said ligating means, wherein said cutting means operates along a predetermined path in the apparatus;
   pusher means for advancing said clip trains and for separating said clips from said clip trains; and
   safety means responsive to said pusher means for preventing said cutting means from cutting said body tissue, wherein said safety means has a means for blocking said path when said safety means responds to said pusher means.

2. The surgical apparatus of claim 1 further comprising:
   a means for restraining said tissue while it is ligated and cut.

3. The surgical apparatus of claim 2, further comprising:
   a means for preventing release of the tissue by the restraining means when the pusher means jams at the completion of a ligating and cutting operation.

4. The surgical apparatus of claim 1, wherein said pusher means operates over a predetermined path to push clips from one end of a channel containing said clip train to apply the clips to said tissue.

5. The surgical apparatus of claim 4, wherein said pusher means engages said safety means when there is no clip at said one end of the channel.

6. The surgical apparatus of claim 5, wherein said safety means comprises a slide movable by said pusher means.

7. The surgical apparatus of claim 6, wherein said slide is at one end engageable with said pusher means and at the other end engageable with said means for cutting.

8. The surgical apparatus of claim 7, wherein said other end forms a blocking spring.

9. The surgical apparatus of claim 8, wherein said blocking spring is engageable with an opening in said cutting means.

10. The surgical apparatus of claim 9, wherein said blocking spring engages a shearing abutment when said blocking spring engages said opening.

11. The surgical apparatus of claim 1, wherein said safety means comprises a slide, one end of which is engageable with said pusher means and the other end of which has a blocking spring movable into said predetermined path.

12. The surgical apparatus of claim 1, wherein said safety means comprises a slide, moveable along a predetermined path, one end of which is engageable with said pusher means and the other end of which is engageable with the means for blocking said means for cutting.

13. The surgical apparatus of claim 12, wherein said blocking means is hairpin shaped having a pair of arms, one of said arms having a projection extending into a slot in said means for cutting when said slide is engaged with said blocking means and extending into an opening in said slot so as to block said means for cutting when said slide is not engaged with said blocking means.

14. The surgical apparatus of claim 13, wherein said projection is resiliently biased towards said opening and said slide prevents said projection from entering said opening when the slide is engaged with said blocking means.

15. The surgical apparatus of claim 14, wherein actuation of said safety means disengages said slide from said blocking means.

16. A surgical apparatus for ligating and cutting organic tissue structures inserted into the apparatus comprising:
    means for simultaneously applying two plastic clips around the tissue structure at two spaced apart locations to ligate the tissue structure at the location of the clips; means for cutting the tissue structure between the clips after said tissue structure has been ligated, wherein said cutting means operates along a predetermined path in the apparatus; and safety means responsive to said applying means for preventing operation of said cutting means, wherein said safety means has a means for blocking said path when said safety means responds to said applying means.

17. The surgical apparatus of claim 16 further comprising:
    a means for restraining said tissue while it is ligated and cut.

18. The surgical apparatus of claim 17, further comprising:
    a means for preventing release of the tissue by the restraining means when the means for applying jams at the completion of a ligating and cutting operation.

19. The surgical apparatus of claim 16, wherein said means for applying operates over a predetermined path to push clips from one end of a channel containing a clip train to apply the clips to said tissue structure.

20. The surgical apparatus of claim 19, wherein said means for applying engages said safety means when there is no clip at said one end of the channel.

21. The surgical apparatus of claim 20, wherein said safety means comprises a slide movable by said means for applying.

22. The surgical apparatus of claim 21, wherein said slide is at one end engageable with said means for applying and at the other end engageable with said means for cutting.

23. The surgical apparatus of claim 22, wherein said other end forms a blocking spring.

24. The surgical apparatus of claim 23, wherein said blocking spring is engageable with an opening in said cutting means.

25. The surgical apparatus of claim 24, wherein said blocking spring engages a shearing means when said blocking spring engages said opening.

26. The surgical apparatus of claim 16, wherein said safety means comprises a slide, one end of which is engageable with said applying means and the other end of which has a blocking spring movable into said predetermined path.

27. The surgical apparatus of claim 16, wherein said safety means comprises a slide, moveable along a predetermined path, one end of which is engageable with said clip applying means and the other end of which is engageable with the means for blocking said means for cutting.

28. The surgical apparatus of claim 27, wherein said blocking means is hairpin shaped having a pair of arms, one of said arms having a projection extending into a slot in said means for cutting when said slide is engaged with said blocking means and extending into an opening in said slot so as to block said means for cutting when said slide is not engaged with said blocking means.

29. The surgical apparatus of claim 28, wherein said projection is resiliently biased towards said opening and said slide prevents said projection from entering said opening when the slide is engaged with said blocking means.

30. The surgical apparatus of claim 29, wherein actuation of said safety means disengages said slide from said blocking means.

31. An instrument for ligating and cutting body tissue having a proximal end and a distal end which comprises:
- a jaw means at the distal end of the instrument for receiving said body tissue;
- a first train of plastic clips extending from the jaw means towards the proximal end of the instrument;
- a second train of plastic clips spaced from said first train extending from the jaw means towards the proximal end of said instrument;
- a pusher means for advancing the distal most clip in each clip train into the jaw means to ligate said body tissue at spaced apart locations;
- a cutting means for dividing said body tissue between said spaced apart locations after it has been ligated, wherein said cutting means operates over a predetermined path in the instrument;
- a means located at the proximal end of the instrument for actuating said pusher means and said cutting means; and
- a safety means responsive to said pusher means for preventing operation of said cutting means, wherein said safety means has a means for blocking said path when said safety means responds to said pusher means.

32. The instrument of claim 31, further comprising:
a means for restraining said tissue in said jaw means during ligation and cutting.

33. The instrument of claim 32, further comprising:
means for preventing removal of said tissue from said jaw means and restraining means when said pusher means jams after ligation and cutting.

34. A surgical instrument for ligating and cutting body tissue, having proximal and distal ends, comprising:
- actuating means at the proximal end of the instrument;
- restraining means at the distal end of the instrument;
- a cartridge connecting said actuating means and said restraining means;
- said actuating means including a handle and a trigger;
- said restraining means comprising two pairs of spaced apart jaws fixed to said cartridge and means for enclosing the space formed by each pair of jaws;
- said cartridge having two channels, each channel extending from the proximal end of the instrument to the distal end of the instrument and containing a train of plastic clips, each clip connected to the clips preceding and following it in the clip train;
- said cartridge also having a knife operating along a predetermind path between said clip trains;
- sequencing means connecting said actuating means with said restraining means and said cartridge for first moving said jaws towards said means for enclosing, then advancing the first clip in each clip train to said jaws so as to close each clip about tissue placed in the jaws and then cutting said tissue between said closed clips with said knife; and
- safety means responsive to said sequencing means for preventing the knife from cutting said tissue, wherein said safety means has a means for blocking said path when said safety means responds to said sequencing means.

* * * * *